(12) United States Patent
Copperman et al.

(10) Patent No.: US 11,342,067 B1
(45) Date of Patent: May 24, 2022

(54) METHODS, SYSTEMS, AND DEVICES FOR CACHING AND MANAGING MEDICAL IMAGE FILES

(71) Applicant: Zebre Technologies, Inc., Nashville, TN (US)

(72) Inventors: Ross Copperman, Nashville, TN (US); Bryan Stunkel, Nashville, TN (US); Brent Savoie, Nashville, TN (US)

(73) Assignee: Zebre Technologies, Inc., Nashville, TN (US)

( * ) Notice: Subject to any disclaimer, the term of this patent is extended or adjusted under 35 U.S.C. 154(b) by 0 days.

(21) Appl. No.: 17/576,166

(22) Filed: Jan. 14, 2022

Related U.S. Application Data

(60) Provisional application No. 63/271,865, filed on Oct. 26, 2021.

(51) Int. Cl.

| | |
|---|---|
| *G06Q 10/00* | (2012.01) |
| *G16H 30/40* | (2018.01) |
| *G06T 7/194* | (2017.01) |
| *G16H 50/20* | (2018.01) |
| *G06T 1/60* | (2006.01) |

(52) U.S. Cl.
CPC ............. *G16H 30/40* (2018.01); *G06T 1/60* (2013.01); *G06T 7/194* (2017.01); *G16H 50/20* (2018.01); *G06T 2207/20081* (2013.01); *G06T 2207/30004* (2013.01)

(58) Field of Classification Search
CPC .......... G16H 30/40; G16H 50/20; G06T 1/60; G06T 7/194; G06T 2207/20081; G06T 2207/30004
See application file for complete search history.

(56) References Cited

U.S. PATENT DOCUMENTS

| | | | |
|---|---|---|---|
| 8,634,677 B2 | 1/2014 | Hu et al. | |
| 10,357,183 B2 * | 7/2019 | Marentis | ............... A61B 90/39 |

(Continued)

FOREIGN PATENT DOCUMENTS

CN 106296518 A * 1/2017

OTHER PUBLICATIONS

Rahmat, Romi Fadillah et al.: "Analysis of DICOM Image Compression Alternative Using Huffman Coding", Hindawi, Journal of Healthcare Engineering, vol. 2019, Jun. 17, 2019, Article ID 5810540, 11 pages, https://doi.org/10.1155/2019/5810540.

(Continued)

*Primary Examiner* — Xin Jia
(74) *Attorney, Agent, or Firm* — NK Patent Law

(57) ABSTRACT

Disclosed herein are methods, systems, and devices for solving the problem of caching large medical images during workflow. In one embodiment, a method is implemented on at least one computing device. The method includes receiving a source medical image file from a first remote device; caching the source medical image file in local memory; determining relevant medical image data, first non-relevant medical image data, and second non-relevant medical image data within the source medical image file; removing the second non-relevant medical image data to create a memory reduced medical image file; storing the memory reduced medical image file in the local memory; and transmitting the memory reduced medical image file to a second remote device.

20 Claims, 22 Drawing Sheets

(56) References Cited

U.S. PATENT DOCUMENTS

| | | | |
|---|---|---|---|
| 2010/0138240 A1* | 6/2010 | Leib | G16H 50/20 |
| | | | 382/128 |
| 2013/0024382 A1* | 1/2013 | Dala | H04L 63/0464 |
| | | | 705/51 |
| 2020/0160980 A1* | 5/2020 | Lyman | G06N 3/0454 |

OTHER PUBLICATIONS

Varma, Dandu Ravi: "Managing DICOM images: Tips and tricks for the radiologist", Indian Journal of Radiology and Imaging, Feb. 2012, vol. 22, Issue 1, 10 pages.

Aspose: "Remove DICOM background for free", Version 21.52, Jan. 25, 2021, https://products.aspose.app/imaging/remove-background/dicom.

Imagemagick: "Background removal from reference image", Jul. 13, 2017, https://legacy.imagemagick.org/discourse-server/viewtopic.php?t=32305.

Peakd: "Remove Background from Multiple Images", Apr. 2, 2020, https://peakd.com/photoshop/@mes/remove-background-from-multiple-images.

\* cited by examiner

IMAGE
600A

IMAGE
600B

IMAGE
700A

IMAGE
700B

METHODS, SYSTEMS, AND DEVICES FOR CACHING AND MANAGING MEDICAL IMAGE FILES

PRIORITY CLAIM

This application claims priority to U.S. Provisional Patent Application Ser. No. 63/271,865 filed Oct. 26, 2021, titled "METHODS, SYSTEMS, AND DEVICES FOR CACHING MEDICAL IMAGE FILES", the disclosure of which is incorporated herein by reference in its entirety.

TECHNICAL FIELD

The present invention relates generally to image management systems. More specifically; methods, systems, and devices are disclosed for caching, storing, and managing medical image files.

BACKGROUND

A Picture Archiving and Communication System (PACS) server provides both short and long term storage of medical images including distribution, retrieval, management and presentation. Medical images may be sources from computerized tomography (CT) scans, magnetic resonance imaging (MRI) scans, ultrasounds, digital X-rays, or the like. A PACS server can support many simultaneous PACS clients. However, a PACS server is typically restricted to a single location and/or department. A vendor neutral archive (VNA) provides both short and long term storage of medical images while providing inter-department access across multiple locations. For 2022, the combined medical artificial intelligence (AI), VNA, and PACS markets are projected to be over $12 billion. By 2027, the combined medical AI, VNA, and PACS markets are expected to reach $70 billion.

However, caching and storing of the medical images during PACS based and VNA based workflow can require large amounts of memory and utilization of network resources during transfer to client devices. As such, new methods, systems, and devices are needed to better manage caching and storage of medical images.

SUMMARY

Disclosed herein are methods, systems, and devices for solving the problem of caching large medical images during workflow. In one embodiment, a method is implemented on at least one computing device. The method includes (1) receiving a source image file from a first remote device; (2) caching the source image file in local memory; (3) creating a memory reduced image file in local memory, and (4) upon receiving a request from a second remote device, transmitting the memory reduced image file to the second remote device. The memory reduced image file is based on the source image file.

In some embodiments, the source image file may be a medical image file.

In some embodiments, the medical image file may be compliant to at least one version of a Digital Imaging and Communications in Medicine (DICOM) format. In other embodiments, the medical image file may be compliant to at least one version of a Neuroimaging Informatics Technology Initiative (NIfTI) format.

In some embodiments, the medical image file may be based on X-ray radiography, magnetic resonance imaging, ultrasound, endoscopy, elastography, tactile imaging, thermography, medical photography, a nuclear medicine functional imaging technique, and or the like. In certain embodiments, the nuclear medicine functional imaging technique may include positron emission tomography (PET), single-photon emission computed tomography (SPECT), or the like.

In some embodiments, the medical image file may be based on non-image data. In certain embodiments, the non-image data may be graphing data, mapping data, and/or the like. In further embodiments, the non-image data may be captured using electroencephalography (EEG), magnetoencephalography (MEG), electrocardiography (ECG), and/or the like.

In some embodiments, the second remote device may be a medical diagnostic workstation, a personal computer, a smart phone, a smart tablet, a smart watch, a smart television (TV), a holographic projector, a two dimensional printer, a three dimensional printer, a transfer device for a portable storage device, and/or the like. In certain embodiments, the portable storage device may be a compact disc (CD), a digital versatile/video disc (DVD), a pen drive, a flash memory card, and/or the like.

In some embodiments, creating the memory reduced image file in the local memory may include determining relevant image data and non-relevant image data within the source image file; removing the non-relevant image data to create the memory reduced image file; and storing the memory reduced image file in the local memory. In further embodiments, creating the memory reduced image file in the local memory may further include replacing the non-relevant image data with a transparent background.

In some embodiments, the second remote device may be configured to replace the transparent background with a solid background to create a memory expanded image file compliant to an image format of the source image file. In certain embodiments, the solid background may be a substantially black background.

In some embodiments, determining relevant image data and non-relevant image data within the source image file may include machine learning. In certain embodiments, the machine learning may include deep learning.

In some embodiments, the method may further include authenticating the second remote device. In certain embodiments, authenticating the second remote device may be based on a challenge-handshake authentication protocol (CHAP), a password authentication protocol (PAP), an extensible authentication protocol/transport layer security (EAP/TLS) protocol, a remote authentication dial-in user service (RADIUS), and/or the like.

In some embodiments, the method may include of claim 12 further authenticating the first remote device. In certain embodiments, authenticating the first remote device may be based on a CHAP, a PAP, an EAP/TLS protocol, a RADIUS, and/or the like.

In some embodiments, the method may further include storing the source image file in a database associated with the at least one computing device.

In some embodiments, the method may further include transmitting the source image file to a third remote device.

In some embodiments, the method may further include authenticating the third remote device. In certain embodiments, authenticating the third remote device may be based on a CHAP, a PAP, an EAP/TLS protocol, a RADIUS, and/or the like.

In some embodiments, the third remote device may be a picture archiving and communication system (PACS) server.

In certain embodiments, the at least one computing device may a PACS caching gateway server.

In some embodiments, the first remote device may be an image modality device. In certain embodiments, the image modality device may be an X-ray device, a computed tomography (CT) scanner, a magnetic resonance imaging (MRI) device, and/or the like. In other embodiments, the first remote device may be a medical image scanner.

In some embodiments, the second remote device may include a PACS viewer.

In some embodiments, the source image file may be a video image file.

In some embodiments, the memory reduced image file may yield a greater than 40 percent digital data reduction over the source image file. In further embodiments, the memory reduced image file may yield a greater than 50 percent digital data reduction over the source image file. In still further embodiments, the memory reduced image file may yield a greater than 60 percent digital data reduction over the source image file. In still further embodiments, the memory reduced image file may yield a greater than 70 percent digital data reduction over the source image file.

In some embodiments, the source image file may be received from the first remote device over an internet protocol (IP) network.

In some embodiments, the memory reduced image file is transmitted to the second remote device over the IP network.

In some embodiments the method may further include deleting the memory reduced image file upon determining a workflow has been completed. In further embodiments, the method may further include triggering a billing event upon deleting the memory reduced image file. In still further embodiments, the method may include transmitting a message to a hospital information system (HIS), a radiology information system (RIS), and/or the like to trigger the billing event.

In another embodiment, a computing device is disclosed. The computing device includes a memory and processor. The processor is configured for (1) receiving a source image file from a first remote device; (2) caching the source image file in local memory; (3) creating a memory reduced image file in local memory, and (4) upon receiving a request from a second remote device, transmitting the memory reduced image file to the second remote device. The memory reduced image file is based on the source image file.

In another embodiment, a non-transitory computer-readable storage medium is disclosed. The non-transitory computer-readable storage medium includes instructions to be implemented on at least one computing device including at least one processor. The instructions when executed by the at least one processor to perform a method. The method includes (1) receiving a source image file from a first remote device; (2) caching the source image file in local memory; (3) creating a memory reduced image file in local memory, and (4) upon receiving a request from a second remote device, transmitting the memory reduced image file to the second remote device. The memory reduced image file is based on the source image file.

In another embodiment, a method is implemented on at least one computing device. The method includes (1) retrieving a source image file from a database associated with the at least one computing device; (2) caching the source image file in local memory; (3) creating a memory reduced image file in local memory; and (4) upon receiving a request from a remote device, transmitting the memory reduced image file to the remote device. The memory reduced image file is based on the source image file.

In another embodiment, a computing device is disclosed. The computing device includes a memory and processor. The processor is configured for (1) retrieving a source image file from a database associated with the at least one computing device; (2) caching the source image file in local memory; (3) creating a memory reduced image file in local memory; and (4) upon receiving a request from a remote device, transmitting the memory reduced image file to the remote device. The memory reduced image file is based on the source image file.

In another embodiment, a non-transitory computer-readable storage medium is disclosed. The non-transitory computer-readable storage medium includes instructions to be implemented on at least one computing device including at least one processor. The instructions when executed by the at least one processor to perform a method. The method includes (1) retrieving a source image file from a database associated with the at least one computing device; (2) caching the source image file in local memory; (3) creating a memory reduced image file in local memory; and (4) upon receiving a request from a remote device, transmitting the memory reduced image file to the remote device. The memory reduced image file is based on the source image file.

In another embodiment, a method is implemented on at least one computing device. The method includes receiving a source medical image file from a first remote device; caching the source medical image file in local memory; determining relevant medical image data, first non-relevant medical image data, and second non-relevant medical image data within the source medical image file; removing the second non-relevant medical image data to create a memory reduced medical image file; storing the memory reduced medical image file in the local memory; and transmitting the memory reduced medical image file to a second remote device.

In some embodiments, the first non-relevant medical image data may include a buffer positioned around the relevant medical image data. In further embodiments, the buffer may be approximately 0.1 to 0.6 centimeters. In still further embodiments, the buffer may be approximately 0.5 to 1.1 centimeters. In still further embodiments, the buffer may be approximately 1.0 to 1.6 centimeters.

In some embodiments, the method may further include replacing the second non-relevant medical image data with a transparent background.

In some embodiments, the second remote device may be configured to replace the transparent background with a solid background to create a memory expanded medical image file compliant to an image format of the source medical image file.

In some embodiments, the solid background may be a substantially black background.

In some embodiments, determining the relevant medical image data, the first non-relevant medical image data, and the second non-relevant medical image data within the source medical image file may include machine learning. The machine learning may include deep learning.

In another embodiment, a computing device is disclosed. The computing device includes a memory and processor. The processor is configured for receiving a source medical image file from a first remote device; caching the source medical image file in local memory; determining relevant medical image data, first non-relevant medical image data, and second non-relevant medical image data within the source medical image file; removing the second non-relevant medical image data to create a memory reduced medical image file; storing the memory reduced medical image file in the local memory; and transmitting the memory reduced medical image file to a second remote device.

In another embodiment, a non-transitory computer-readable storage medium is disclosed. The non-transitory computer-readable storage medium includes instructions to be implemented on at least one computing device including at least one processor. The instructions when executed by the at least one processor to perform a method. The method includes receiving a source medical image file from a first remote device; caching the source medical image file in local memory; determining relevant medical image data, first non-relevant medical image data, and second non-relevant medical image data within the source medical image file; removing the second non-relevant medical image data to create a memory reduced medical image file; storing the memory reduced medical image file in the local memory; and transmitting the memory reduced medical image file to a second remote device.

The features and advantages described in this summary and the following detailed description are not all-inclusive. Many additional features and advantages will be apparent to one of ordinary skill in the art in view of the drawings, specification, and claims presented herein.

BRIEF DESCRIPTION OF THE DRAWINGS

The present embodiments are illustrated by way of example and are not intended to be limited by the figures of the accompanying drawings. In the drawings:

FIG. 22 depicts a diagram illustrating another GUI within the ZEBRE COORDINATE™ application in accordance with embodiments of the present disclosure.

DETAILED DESCRIPTION

Figure 1:
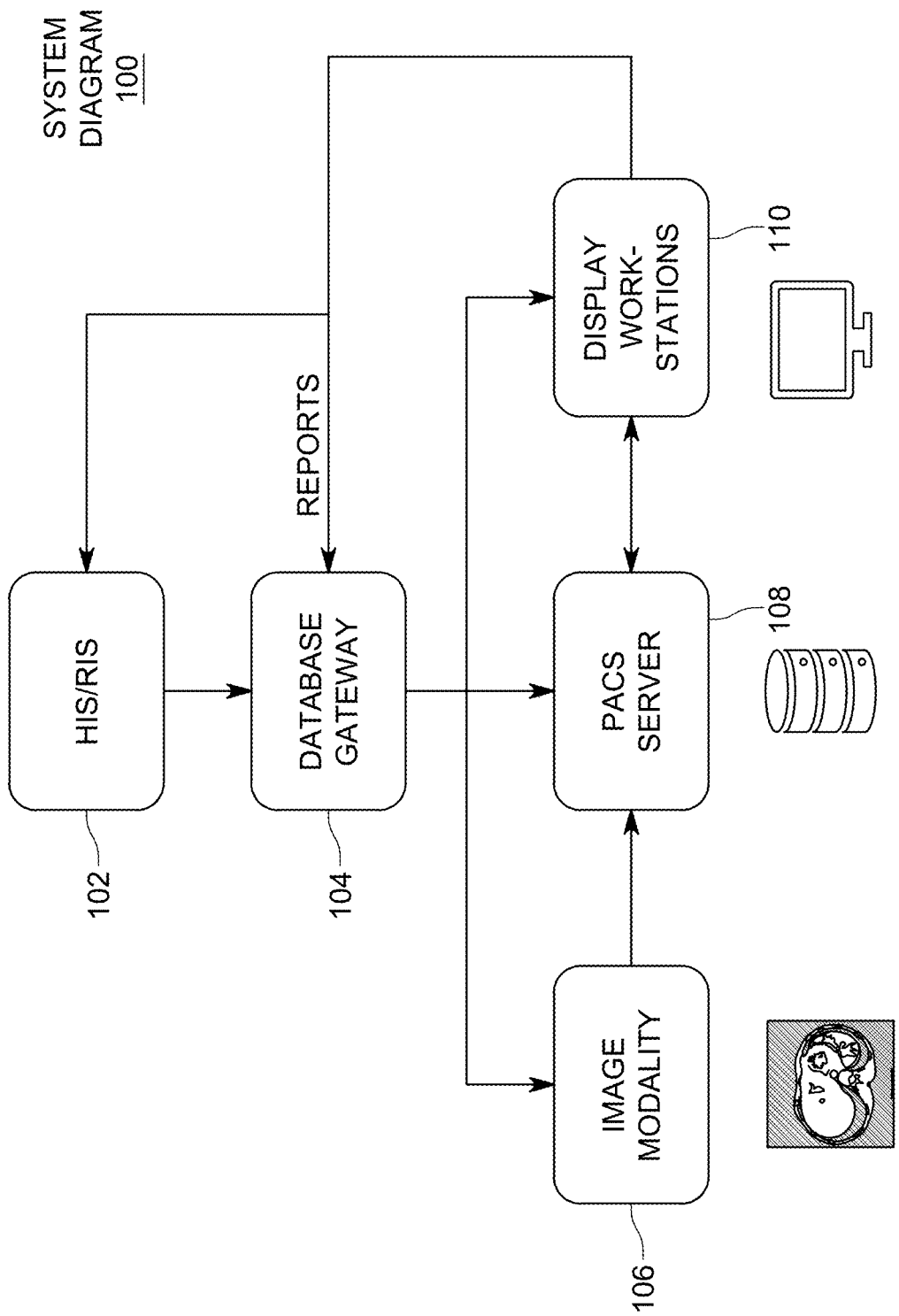
FIG. 1 depicts a system diagram illustrating a traditional medical imaging architecture in accordance with embodiments of the present disclosure.

The following description and drawings are illustrative and are not to be construed as limiting. Numerous specific details are described to provide a thorough understanding of the disclosure. However, in certain instances, well-known or conventional details are not described in order to avoid obscuring the description. References to "one embodiment" or "an embodiment" in the present disclosure can be, but not necessarily are, references to the same embodiment and such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and is not intended to further limit the scope and meaning of the disclosure or of any exemplified term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

Medical image files can very large frequently measuring over a gigabyte (GB). As such medical imaging databases may consume petabytes of data. A large percentage of this data is either duplicative or non-diagnostic and running as high as 75% for data intensive imaging modalities such as CT scans.

Data clutter and data waste taxes the medical data infrastructure increasing storage costs, latency, transmission costs. Data clutter also limits the ability of health care systems to leverage emerging technologies—including 5G-enabled transmission of medical imaging files and transmitting optimized files to cloud-based artificial intelligence (AI) and machine learning (ML) applications.

The present invention relates to methods, systems, and devices for solving the problem of caching large medical images during workflow while reducing memory footprints for long term storage. Specifically, ZEBRE TECHNOLOGIES™ solutions are disclosed for complimenting Picture Archiving and Communication System (PACS) platforms. The ZEBRE TECHNOLOGIES™ solutions include a software application and a software plug-in as separate solutions to reside on a PACS server. Additionally, the ZEBRE TECHNOLOGIES™ solutions include a proxy server to compliment a PACS server. The ZEBRE TECHNOLOGIES™ solutions allow the size of medical image files to be reduced while cached for workflow in a substantially lossless manner. In addition to PACS servers, the ZEBRE TECHNOLOGIES™ solutions apply to vendor neutral archives (VNAs), and other medical image storage systems like those that may be associated with AI and ML storage related to medical imaging.

FIG. 1 depicts a system diagram 100 illustrating a traditional medical imaging architecture in accordance with embodiments of the present disclosure. The traditional medical imaging architecture includes hospital information systems and radiology information systems (HIS/RIS) 102, a database gateway 104, image modality 106, a PACS server 108, and display workstations 110. Devices associated with the image modality 106 may include X-ray devices, computed tomography (CT) scanners, magnetic resonance imaging (MRI) devices, and/or the like.

As previously described medical imaging files are large and require much memory while cached during workflow. The ZEBRE TECHNOLOGIES™ solutions remove non-relevant digital data from the medical images while cached reducing memory requirements and network bandwidth needed during workflow. For example, a Digital Imaging and Communications in Medicine (DICOM) format file may be reduced over 50 percent with one of the ZEBRE TECHNOLOGIES™ solutions. With multiple ZEBRE TECHNOLOGIES™ solutions a DICOM formatted file series may be reduced over 75 percent.

Figure 2:
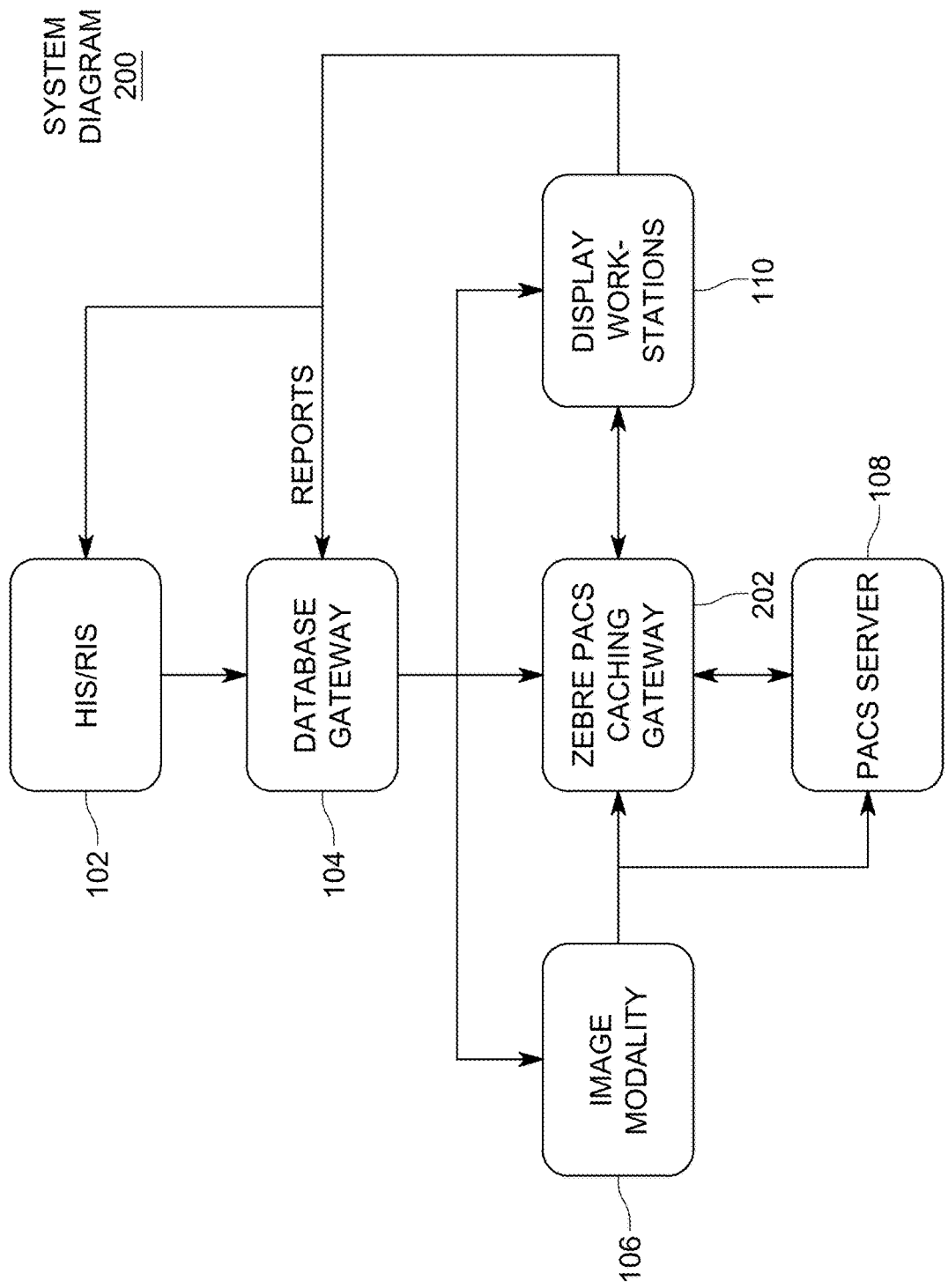
FIG. 2 depicts a system diagram illustrating the traditional medical imaging architecture of FIG. 1 using a ZEBRE TECHNOLOGIES™ picture archiving and communication system (PACS) caching gateway in accordance with embodiments of the present disclosure.

FIG. 2 depicts a system diagram 200 illustrating the traditional medical imaging architecture of FIG. 1 using a ZEBRE TECHNOLOGIES™ PACS caching gateway 202 in accordance with embodiments of the present disclosure.

Figure 3:
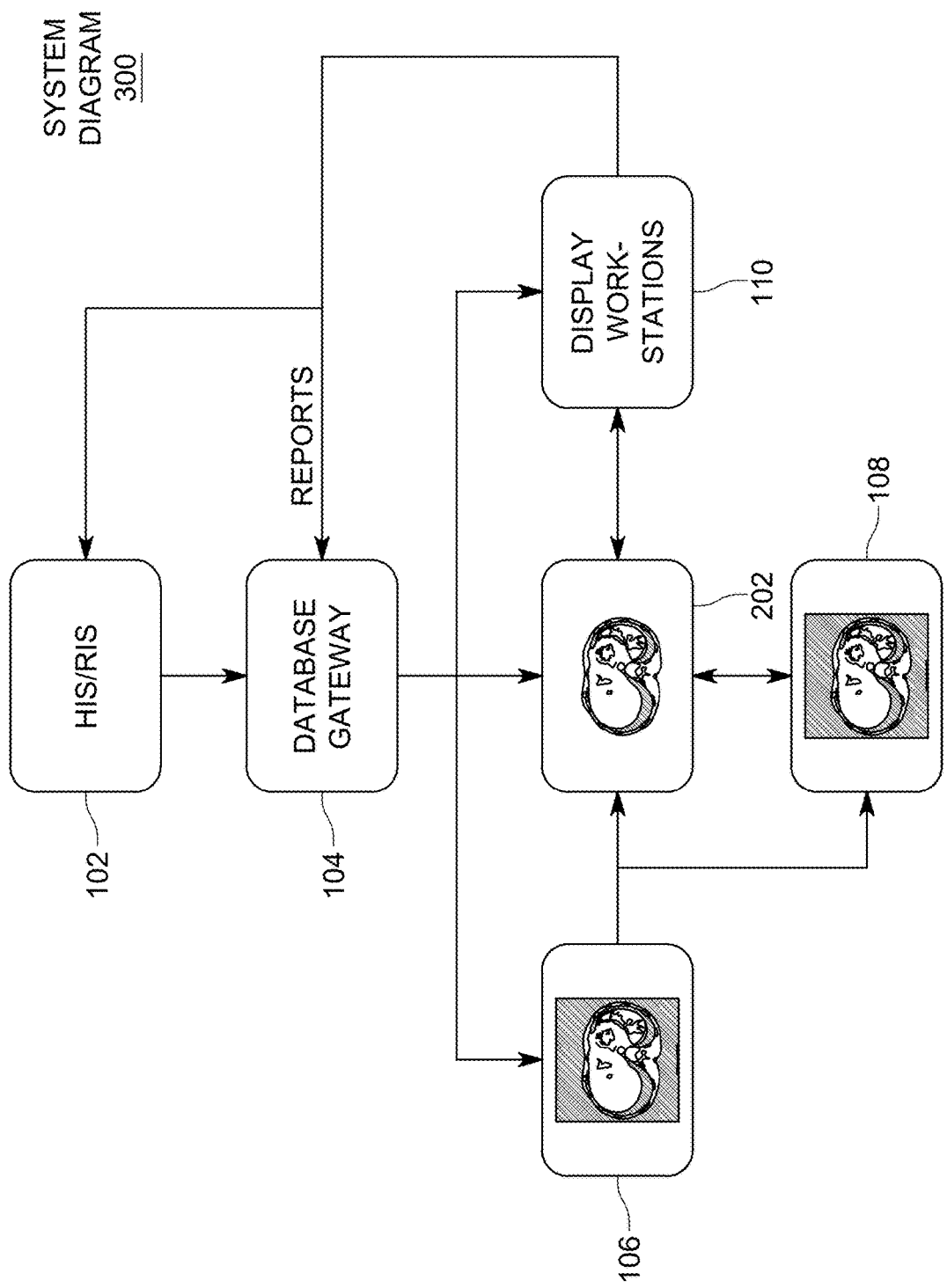
FIG. 3 depicts a system diagram illustrating image sizes within an image modality, a PACS server, and the ZEBRE TECHNOLOGIES™ PACS caching gateway of FIG. 2 in accordance with embodiments of the present disclosure.

FIG. 3 depicts a system diagram 300 further illustrating the image sizes within image modality 106, the PACS server 108, and the ZEBRE TECHNOLOGIES™ PACS caching gateway 202 of FIG. 2 in accordance with embodiments of the present disclosure.

Figure 4:
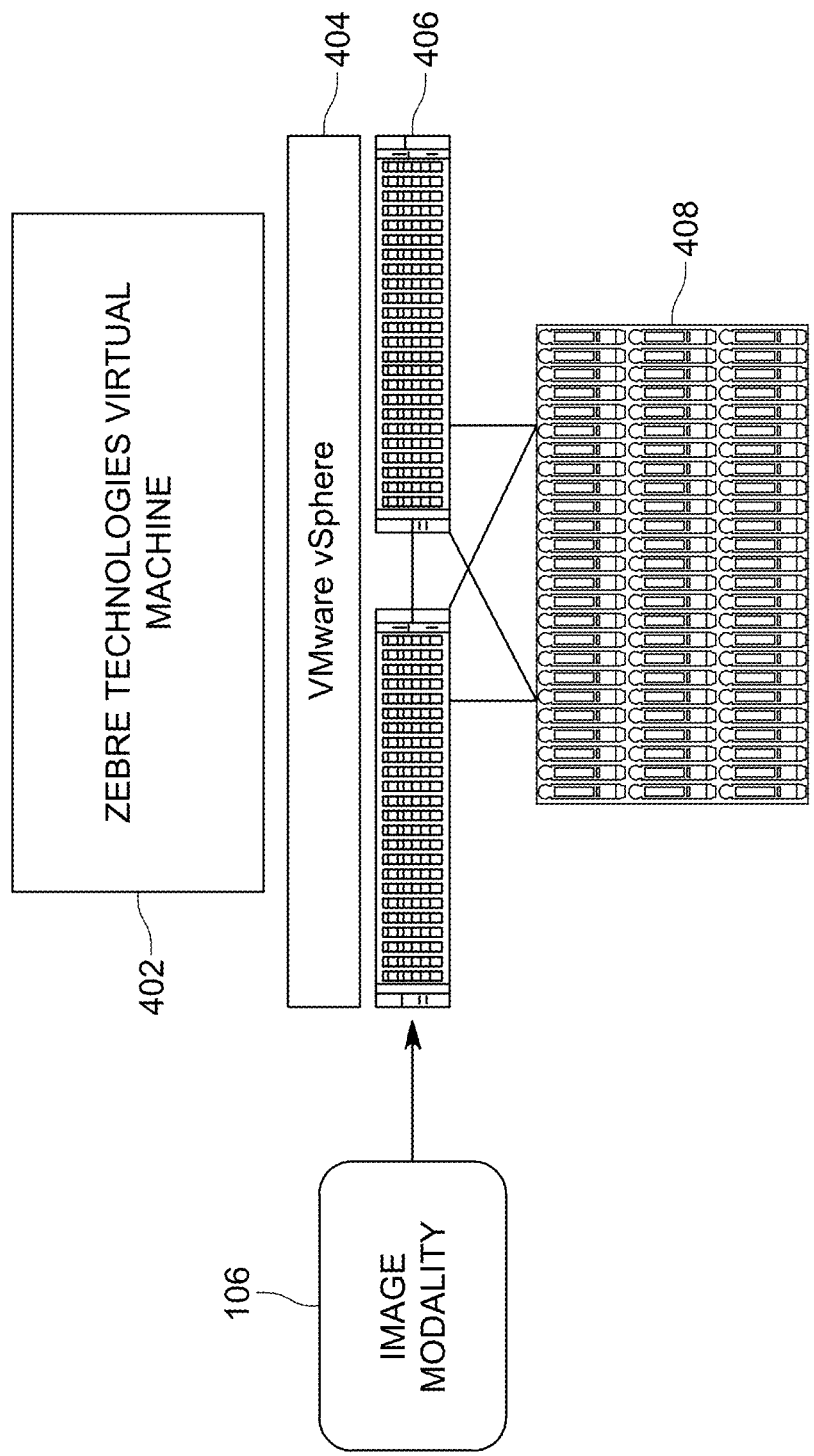
FIG. 4 depicts a system diagram illustrating a ZEBRE TECHNOLOGIES™ software application (i.e. ZEBRE TECHNOLOGIES™ source image extraction use case) for reducing needed memory during caching of medical images on a PACS server in accordance with embodiments of the present disclosure.

FIG. 4 depicts a system diagram 400 illustrating a ZEBRE TECHNOLOGIES™ software application 402 (i.e. ZEBRE TECHNOLOGIES™ source image extraction use case) for reducing needed memory during caching of medical images on a PACS server in accordance with embodiments of the present disclosure. The system diagram 400 also includes the image modality 106 of FIG. 1 and FIG. 2. The system diagram 400 further includes a VMware® vSphere virtual server 404, tier one storage 406, and tier two storage 408. The tier one storage 406 may include local server solid state device (SSD) storage and/or non-volatile memory express (NVMe) SSD device storage. The tier two storage 408 may include PACS based Serial-Attached Small Computer System Interface (SAS) interface storage devices and/or Serial AT Attachment (SATA) interface storage devices.

The ZEBRE software application 402 is installed on an existing PACS server. A source image (e.g. a DICOM image) is ingested into the ZEBRE TECHNOLOGIES™ software application 402 from the image modality 106. The non-relevant information is removed and the reduced memory image is cached in the tier one storage 406 for ongoing workflow. Additionally, the source image is ingested from the image modality 106 to the tier two storage 408. The source image remains in the tier two storage 408 in its original format.

The ZEBRE TECHNOLOGIES™ software application 402 keeps the reduced memory image cached in the tier one storage 406 until review workflow is complete. Once workflow is complete, the ZEBRE software application 402 deletes the reduced memory image from the memory cache and only the source image (i.e. golden image) remains in the tier two storage 408. Additionally, the ZEBRE software application 402 may trigger billing workflow when deleting cached memory reduced images.

The ZEBRE TECHNOLOGIES™ software application 402 as described in FIG. 4 may apply as an add on software application for Sectra® systems, Intelerad® Medical Systems, AGFA® systems, and/or the like.

Figure 5:
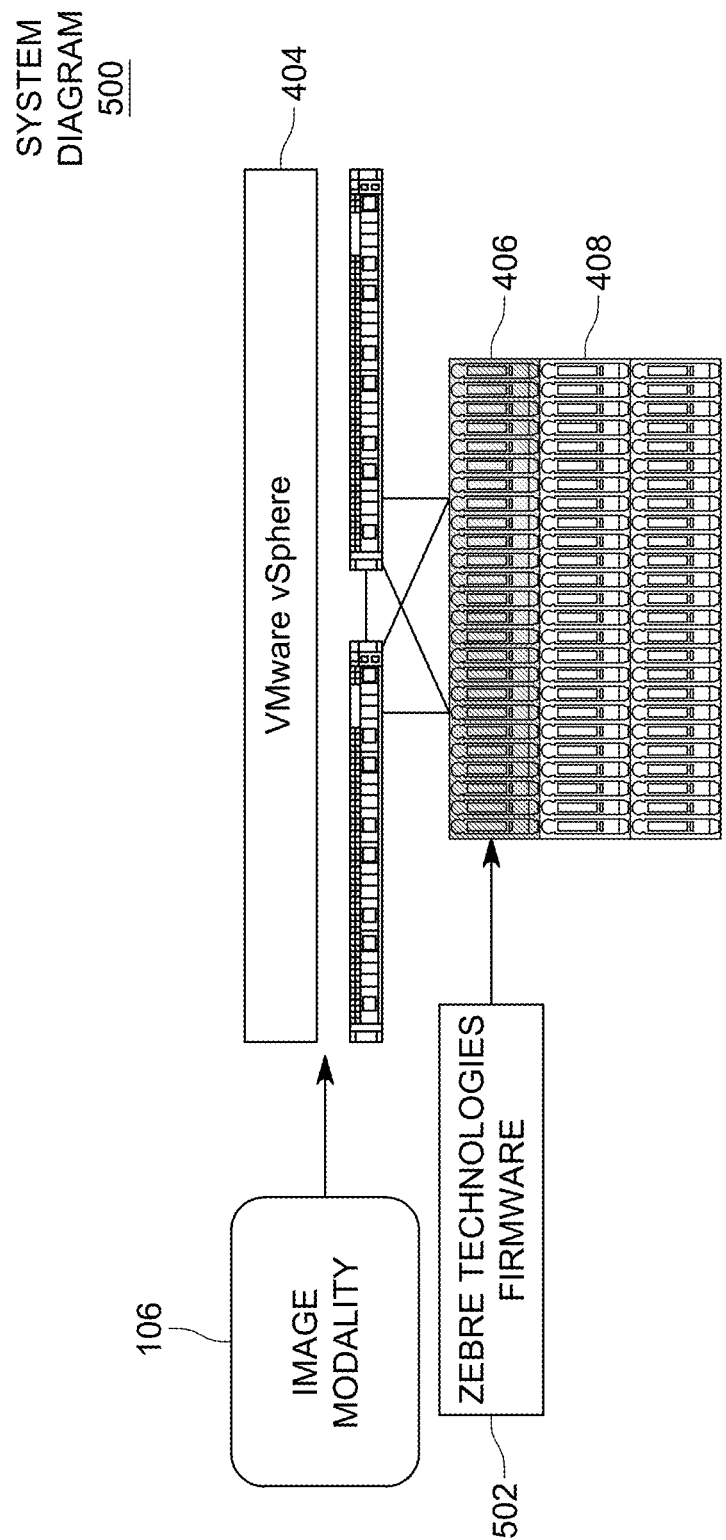
FIG. 5 depicts a system diagram illustrating a ZEBRE TECHNOLOGIES™ software plugin 502 (i.e. ZEBRE TECHNOLOGIES™ target image extraction use case) for reducing needed memory during caching of medical images on a PACS server in accordance with embodiments of the present disclosure.

FIG. 5 depicts a system diagram 500 illustrating a ZEBRE TECHNOLOGIES™ software plugin 502 (i.e. ZEBRE TECHNOLOGIES™ target image extraction use case) for reducing needed memory during caching of medical images on a PACS server in accordance with embodiments of the present disclosure. The system diagram 500 also includes the image modality 106, the VMware® vSphere virtual server 404, the tier one storage 406, and the tier two storage 408 of FIG. 4.

The ZEBRE software plug-in 502 is installed on an existing PACS server and/or storage device as a device driver, a firmware upgrade, and/or the like. Similar to the system 400, a source image (e.g. a DICOM image) is ingested into the ZEBRE TECHNOLOGIES™ software plug-in 502 from the image modality 106. The non-relevant information is removed and the reduced memory image is cached in the tier one storage 406 for ongoing workflow. Additionally, the source image is ingested from the image modality 106 to the tier two storage 408. The source image remains in the tier two storage 408 in its original format.

The ZEBRE TECHNOLOGIES™ software plugin 502 keeps the reduced memory image cached in the tier one storage 406 until review workflow is complete. Once workflow is complete, the ZEBRE TECHNOLOGIES™ software plugin 502 deletes the reduced memory image from the memory cache and only the source image (i.e. golden image) remains in the tier two storage 408. Additionally, the software plugin 502 may trigger billing workflow when deleting cached memory reduced images.

The ZEBRE TECHNOLOGIES™ software plugin 502 as described in FIG. 5 may apply as a device driver and/or a firmware upgrade for a Dell® system, an HPE® system, a Pure Storage®, and/or the like.

Figure 6A:
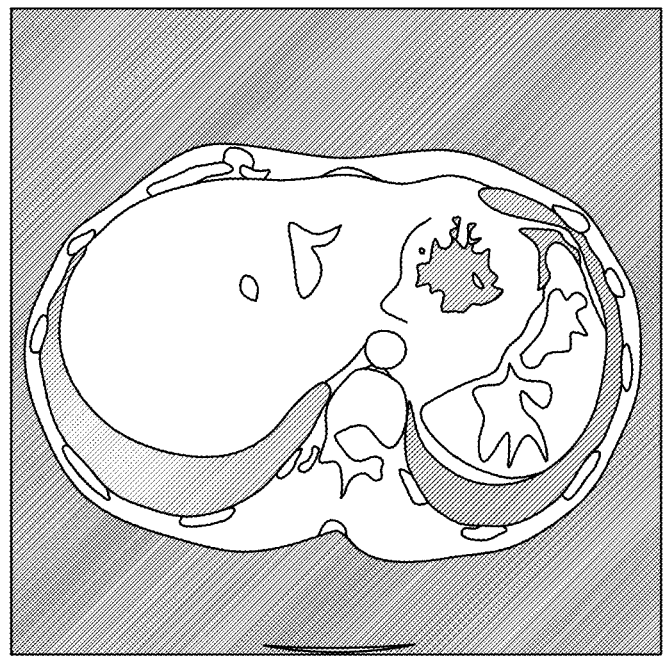
FIG. 6A depicts an image illustrating a typical DICOM image of a gland captured using magnetic resonance imaging in accordance with embodiments of the present disclosure.
Figure 6B:
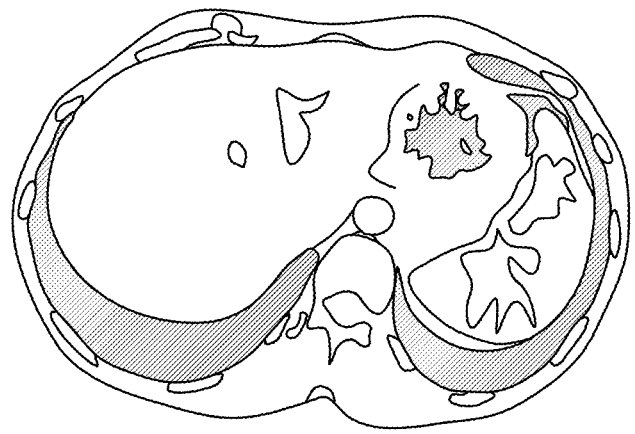
FIG. 6B depicts an image illustrating remaining relevant image data of the image 600A in accordance with embodiments of the present disclosure.

FIG. 6A depicts an image 600A illustrating a typical DICOM image of a gland captured using magnetic resonance imaging in accordance with embodiments of the present disclosure. FIG. 6B depicts an image 600B illustrating remaining relevant image data of the image 600A in accordance with embodiments of the present disclosure. Using one of the ZEBRE TECHNOLOGIES™ solutions (i.e. proxy server, software application, or software plug-in), the black background has been replaced with a transparent background. The image 600B has a greater than 50 percent digital data reduction over the image 600A.

Figure 7A:
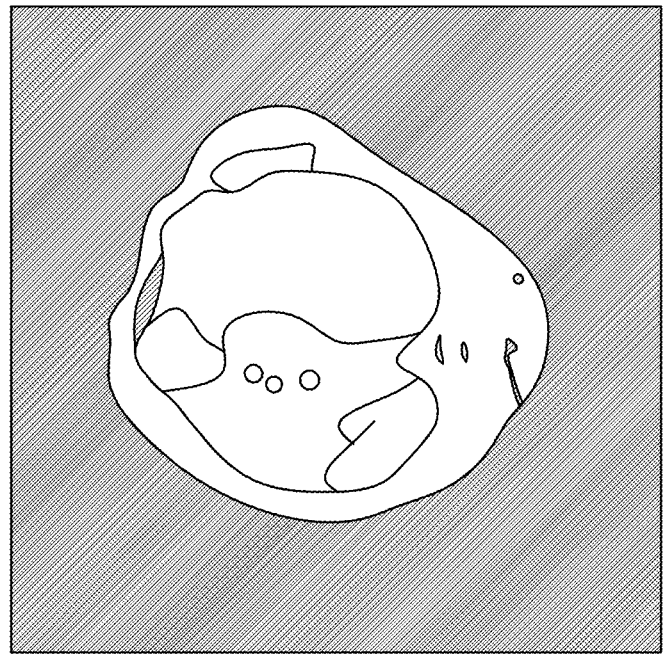
FIG. 7A depicts an image illustrating another typical DICOM image of the gland captured using magnetic resonance imaging in accordance with embodiments of the present disclosure.
Figure 7B:
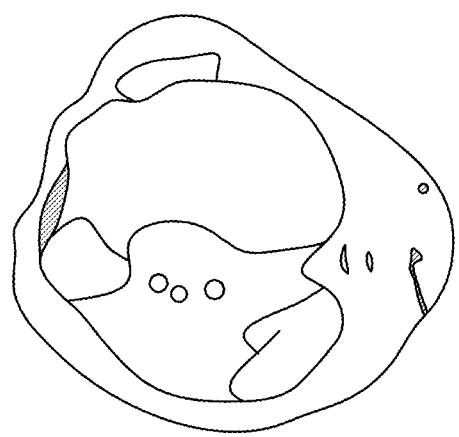
FIG. 7B depicts another image illustrating remaining relevant image data of the image 700A in accordance with embodiments of the present disclosure.

FIG. 7A depicts an image 700A illustrating another typical DICOM image of the gland captured using magnetic resonance imaging in accordance with embodiments of the present disclosure. FIG. 7B depicts an image 700B illustrating remaining relevant image data of the image 700A in accordance with embodiments of the present disclosure. Again using one of the ZEBRE TECHNOLOGIES™ solutions (i.e. proxy server, software application, or software plug-in), the black background has been replaced with a transparent background. The image 700B also has a greater than 50 percent digital data reduction over image 700A.

Figure 8:
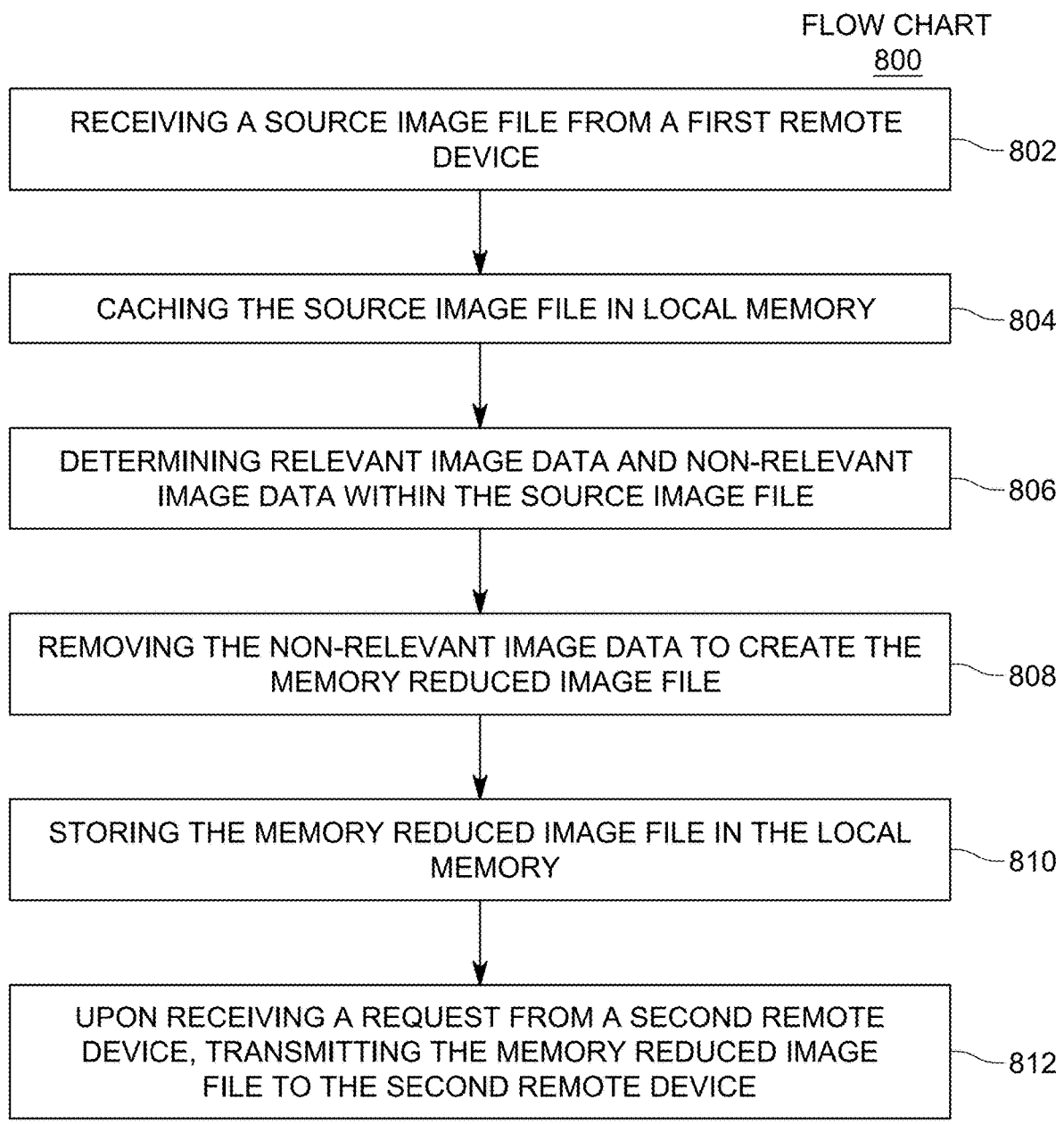
FIG. 8 depicts a flowchart illustrating a method implemented on at least one computing device for reducing memory during caching of images in accordance with embodiments of the present disclosure.

FIG. 8 depicts a flowchart 800 illustrating a method implemented on at least one computing device for reducing memory during caching of images in accordance with embodiments of the present disclosure. Additionally, the method may be stored as instructions on a non-transitory computer-readable storage medium to be implemented on the at least one computing device.

In step 802, the method includes receiving a source image file from a first remote device. The source image file may be received over an Internet protocol (IP) network. The source image file may also be retrieved from a database associated with the at least one computing device. The source image file may be a medical image file compliant to at least one version of a Digital Imaging and Communications in Medicine (DICOM) format. The source image file may also be a medical image file compliant to at least one version of a Neuroimaging Informatics Technology Initiative (NIfTI) format. The source image file may even be a video image file. Additionally, the medical image file may be based on X-ray radiography, magnetic resonance imaging, ultrasound, endoscopy, elastography, tactile imaging, thermography, medical photography, a nuclear medicine functional imaging technique, and or the like. The nuclear medicine functional imaging technique may include positron emission tomography (PET), single-photon emission computed tomography (SPECT), or the like. The medical image file may also be based on non-image data. For example the non-image file may be graphing data, mapping data, and/or the like. The non-image data may be captured using at least one of electroencephalography (EEG), magnetoencephalography (MEG), electrocardiography (ECG), and/or the like.

The first remote device may be an image modality device. For example the first remote device may be an X-ray device, a computed tomography (CT) scanner, a magnetic resonance imaging (MRI) device, and/or the like. In other embodiments, the first remote device may be a medical image scanner to scan paper and/or film based images. Prior to step 802 (not shown if FIG. 8), the method may include authenticating the first remote device over the IP network. For example the authentication may include a challenge-handshake authentication protocol (CHAP), a password authentication protocol (PAP), an extensible authentication protocol/transport layer security (EAP/TLS) protocol, a remote authentication dial-in user service (RADIUS), and/or the like.

In step 804, the method further includes caching the source image file in local memory. The local memory may be the tier one storage 406 as described in FIG. 4 and FIG. 5. Additionally, the source image file may be stored on long-term memory. The long-term memory may be tier two storage 408 as described in FIG. 4 and FIG. 5.

In step 806-810, the method further includes creating a memory reduced image file based on the source image file in local memory. Specifically in step 806, the method further includes determining relevant image data and non-relevant image data within the source image file. Determining the relevant image data and the non-relevant image data within the source image file may include one or more machine learning techniques. The machine learning may also include deep learning techniques. The machine learning may be based on MIScnn, OpenCV, TensorFlow, Caffe, EmguCV, Kornia, and/or the like. The non-relevant image data may include background data of the source image file. Some of the determined non-relevant image data may be reclassified as relevant image data. For example, a few pixels of the background bordering the relevant image data may be reclassified as relevant image data. Depending on a certainty in determining the relevant image data, the pixel border may be adjusted. For example, the pixel border may be between 1 and 10 pixels or between 10 and 100 pixels.

Specifically in step 808, the method further includes removing the non-relevant image data to create the memory reduced image file. For example, the non-relevant image data may be replaced with a transparent background. The relevant image data remains in a loss-less format. The memory reduced image file may be 40, 50, even 60 percent smaller than the source image file.

In step 810, the method further includes storing the memory reduced image file in the local memory. Once the memory reduced image file is stored, the source image file may be deleted from the local memory (e.g. the tier one storage 406).

In step 812, the method further includes upon receiving a request from a second remote device, transmitting the memory reduced image file to the second remote device. The memory reduced image file may be transported over an IP network to the second remote device. The second remote device may be a medical diagnostic workstation, a personal computer, a smart phone, a smart tablet, a smart watch, a smart television (TV), a holographic projector, a two dimensional printer, a three dimensional printer, a transfer device for a portable storage device, and/or the like. The portable storage device may be a compact disc (CD), a digital versatile/video disc (DVD), a pen drive, a flash memory card, and/or the like. The second remote device may include a PACS viewer. The second remote device may be configured to replace the transparent background with a solid background to create a memory expanded image file compliant to an image format of the source image file. For example, the solid background may be a substantially black background. Prior to step 812 (not shown in FIG. 8), the method may include authenticating the second remote device. The authentication may be completed in a manner similar to authenticating the first remote device.

The method may be implemented on the same hardware as the PACS server or may be implemented remotely from the PACS server as a proxy server. In this scenario, the proxy server may communicate with the PACS server over an IP network and authenticate the PACS server in a manner similar to the first remote device. In other embodiments, the PACS server may authenticate the proxy server in a similar manner.

Figure 9:
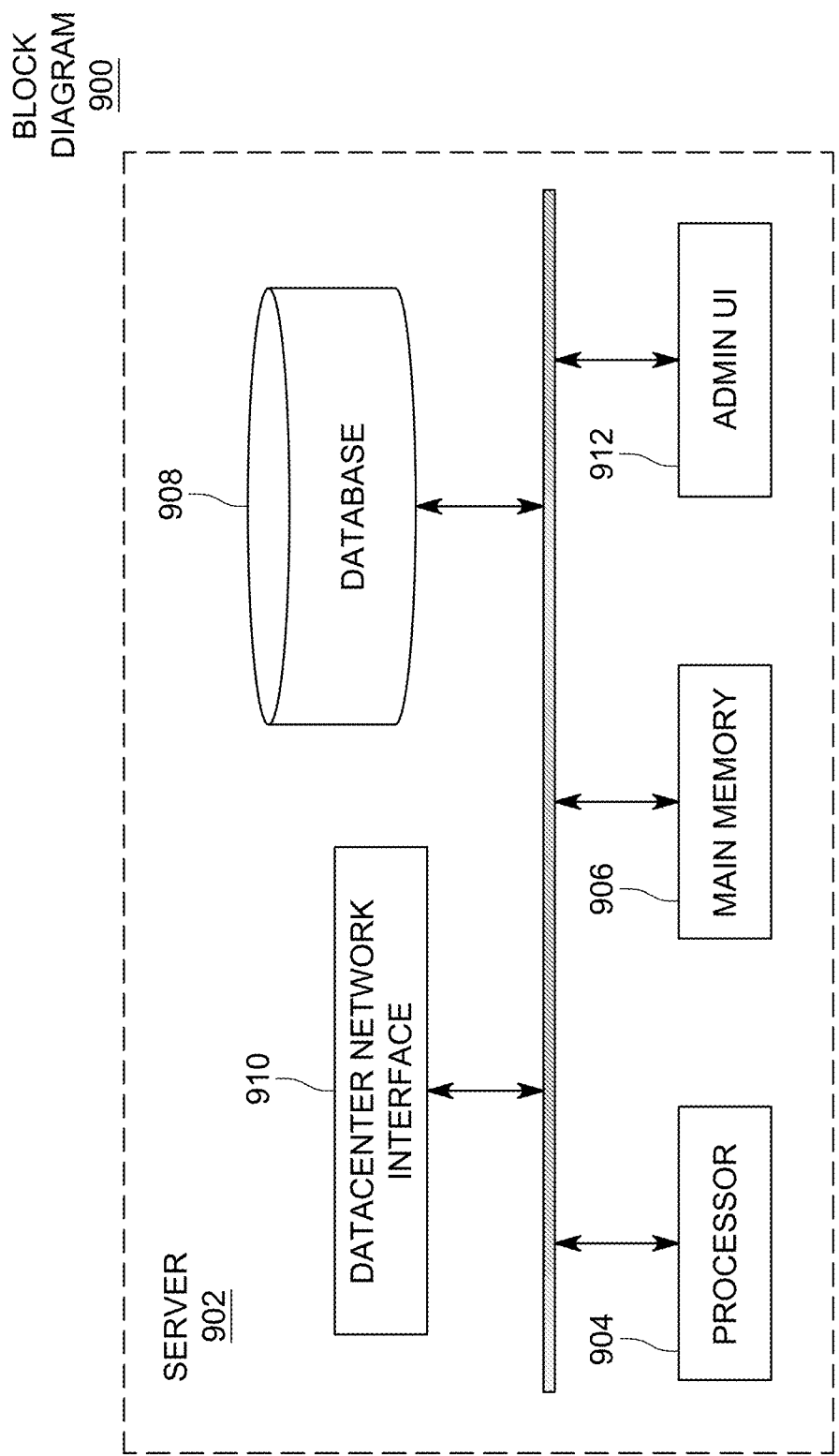
FIG. 9 depicts a block diagram illustrating a server in accordance with embodiments of the present disclosure.

FIG. 9 depicts a block diagram 900 illustrating a server 902 in accordance with embodiments of the present disclosure. The server 902 may provide at least a portion of the hardware platform for a PACS server, a PACS server including the ZEBRE TECHNOLOGIES™ application 402 (see FIG. 4) executing above caching storage tier 406 and the archival storage tier 408, and/or a PACS server including the ZEBRE software plug-in 502 executing between the caching storage tier and the archival storage tier (see FIG. 5). Additionally, the server 902 may provide at least a portion of the hardware platform for a ZEBRE application executing as a proxy server remotely from the PACS server (see FIG. 2).

Additionally, the server 902 may host at least a portion of a virtual server. For example the virtual server may a VMware® vSphere virtual server, an Ubuntu® virtual server, or the like. In other embodiments, the server 902 may host a virtual container, for example a Docker® virtual container. The server may be physically located in a hospital or other medical facility providing a network computing environments. In other embodiments, the server 902 may be implemented in the Microsoft Azure®, the Amazon Web Services® (AWS), or the like cloud computing data center environments.

Figure 10:
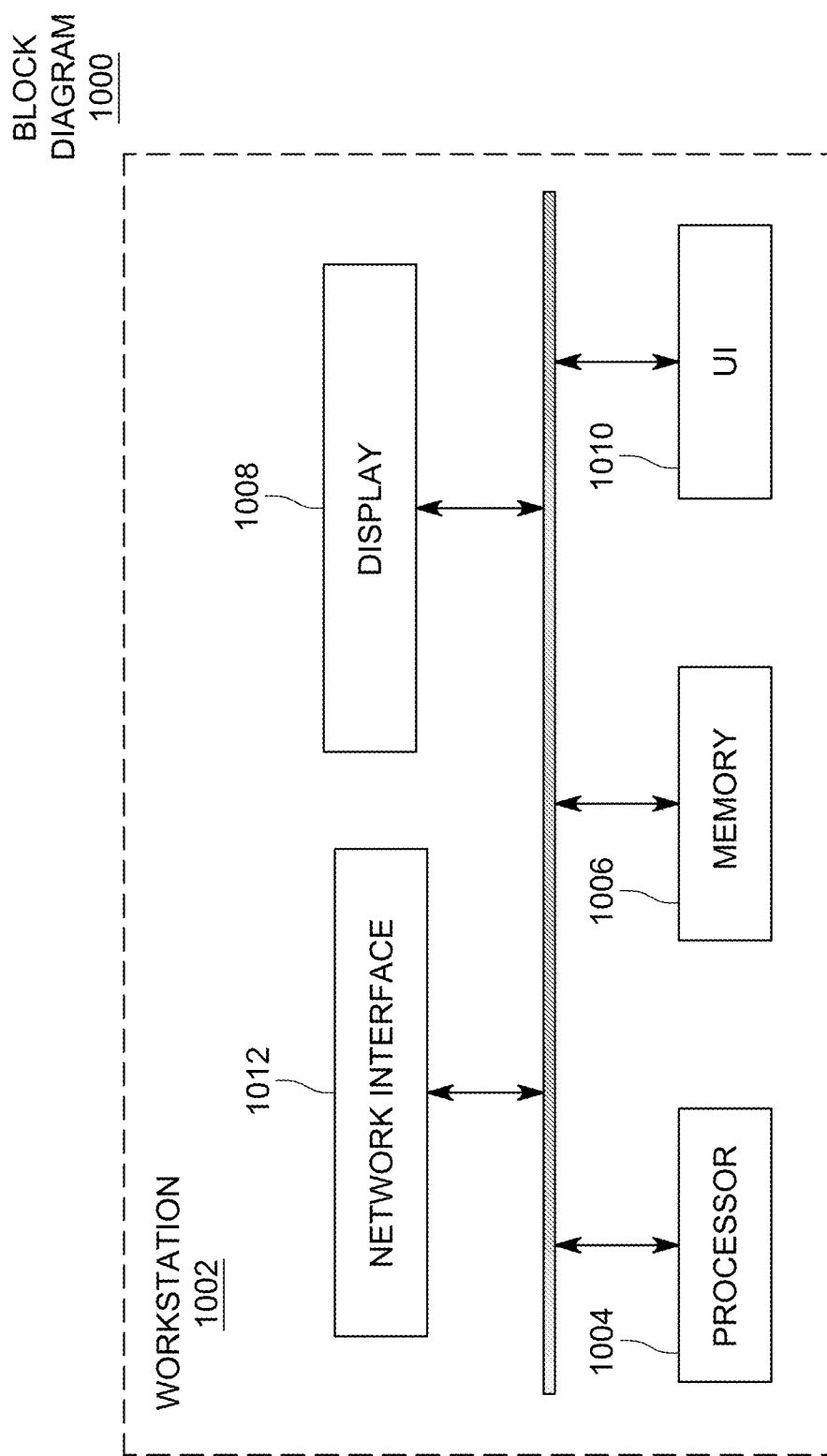
FIG. 10 depicts a block diagram illustrating a workstation in accordance with embodiments of the present disclosure.

The server 902 may include at least one of processor 904, a main memory 906, a database 908, a datacenter network interface 910, and an administration user interface (UI) 710. The server 902 may be configured to host an Ubuntu® server. In some embodiments Ubuntu® server (or other virtual server) may be distributed over a plurality of hardware servers using hypervisor technology. The processor 904 may be a multi-core server class processor suitable for hardware virtualization. The processor may support at least a 64-bit architecture and a single instruction multiple data (SIMD) instruction set. The main memory 906 may include a combination of volatile memory (e.g. random access memory) and non-volatile memory (e.g. flash memory). The database 908 may include one or more hard drives. The database 908 may be an open source database such as the MongoDB® database, the PostgreSQL® database, or the like. The datacenter network interface 910 may provide one or more high-speed communication ports to the data center switches, routers, and/or network storage appliances. The datacenter network interface 910 may include high-speed optical Ethernet, InfiniBand (IB), Internet Small Computer System Interface (iSCSI), and/or Fibre Channel interfaces. The administration UI 912 may support local and/or remote configuration of the server 902 by a datacenter administrator FIG. 10 depicts a block diagram 1000 illustrating a workstation 1002 in accordance with embodiments of the present disclosure. The workstation 1002 may be configured to communicate with the server 902 over a network. The workstation 610 may be configured to host a specific application (e.g. medical image viewer), a browser application, another third party application for utilizing medical images, and/or the like. The workstation 1002 may include at least one processor 1004, a memory 1006, a display 1008, a UI 1010, and a network interface 1012. The workstation 1002 may include an operating system (OS) such as a Windows® OS, a Macintosh® OS, a Linux® OS, or the like. The memory 1006 may include a combination of volatile memory (e.g. random access memory) and non-volatile memory (e.g. solid state drive and/or hard drives). The display 1008 may be an external display (e.g. computer monitor) or internal display (e.g. laptop). The UI 1010 may include a keyboard, and a pointing device (e.g. mouse). The network interface 1012 may be a wired Ethernet interface or a Wi-Fi interface.

Figure 11:
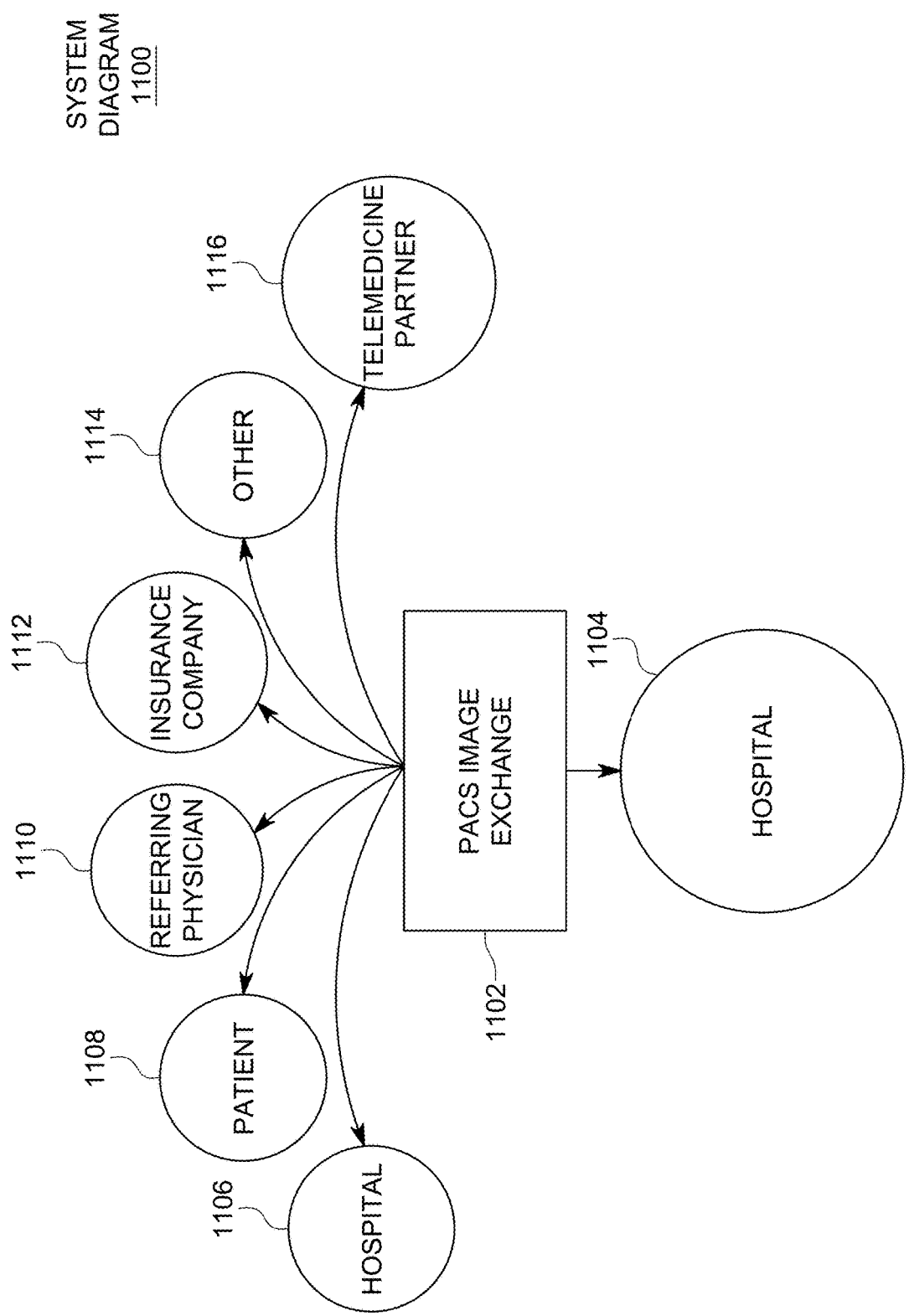
FIG. 11 depicts a system diagram illustrating an embodiment of a traditional PACS image exchange in accordance with embodiments of the present disclosure.

FIG. 11 depicts a system diagram 1100 illustrating an embodiment of a traditional PACS image exchange 1102 in accordance with embodiments of the present disclosure. The PAC image exchange 1102 provides medical imaging between hospitals 1104 and 1106, patients 1108, referring physicians 1110, insurance companies 1112, telemedicine partners 1116, and other entities 1114.

Figure 12:
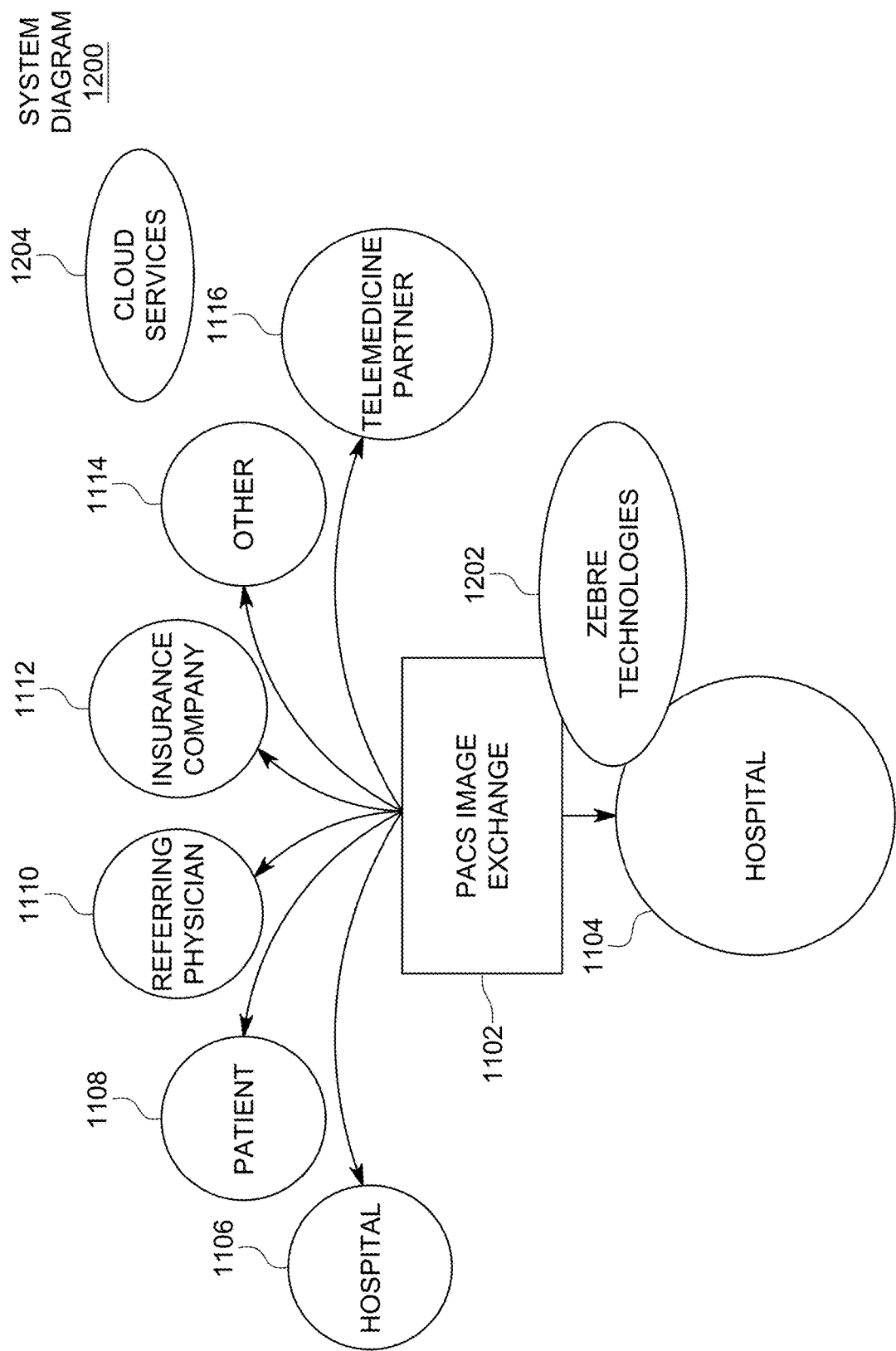
FIG. 12 depicts a system diagram illustrating the PACS image exchange of FIG. 11 utilizing the previously described ZEBRE TECHNOLOGIES™ solutions in accordance with embodiments of the present disclosure.

FIG. 12 depicts a system diagram 1200 illustrating the PACS image exchange 1102 of FIG. 11 utilizing the previously described ZEBRE TECHNOLOGIES™ solutions 1202 and cloud services 1204 in accordance with embodiments of the present disclosure.

The ZEBRE TECHNOLOGIES™ solutions remove wasted storage space of nonessential components (diagnostic information) of medical imaging files. As such, lowering volume of digital data, and enabling efficient transport over the Internet. In general, a digital data reduction greater than 25 to 75 percent can be achieved with the ZEBRE TECHNOLOGIES™ solutions.

In further embodiments, ZEBRE TECHNOLOGIES™ solutions includes the ZEBRE OPTIMIMIZE™ platform comprising two applications that work in parallel to reduce medical imaging data waste and radically decrease file sizes. A first application, ZEBRE CLARITY™ is a series-level optimization application that identifies and eliminates redundant series. The ZEBRE CLARITY™ application (acting alone) can typically achieve a digital data reduction greater than 50 percent on a medical image series. A second application, ZEBRE FOCUS™ is an image-level optimization application that eliminates non-diagnostic data from individual images. The ZEBRE FOCUS™ application (acting alone) can also typically achieve a digital data reduction greater than 50 percent on a given image file. Using both the ZEBRE CLARITY™ application and the ZEBRE FOCUS™ application (acting together) a digital data reduction of 75 percent or greater can be achieved on a given medical image series.

Figure 13:
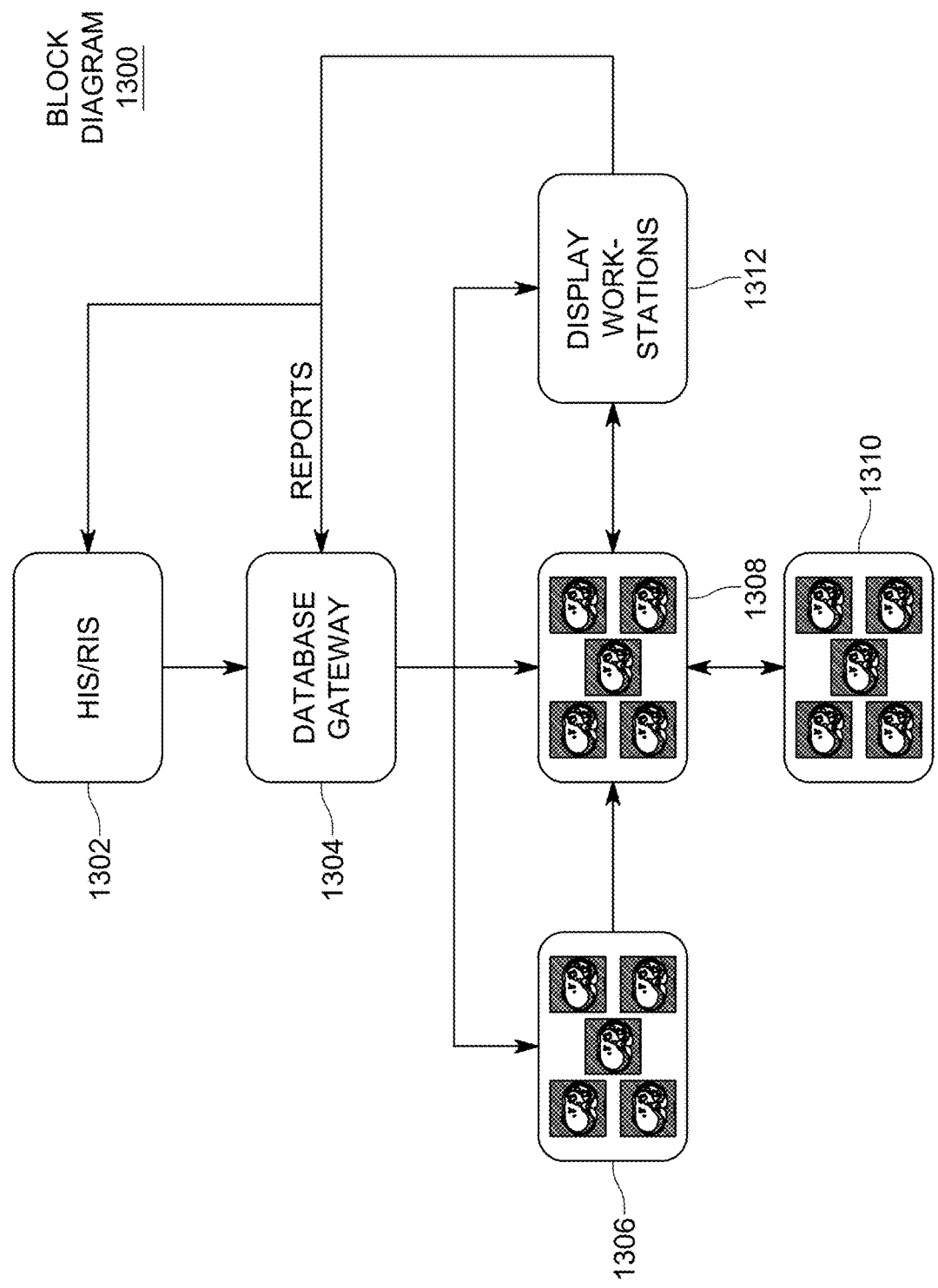
FIG. 13 depicts a block diagram re-illustrating the traditional medical imaging architecture of FIG. 1 further illustrating the redundant caching/storage of complete images in accordance with embodiments of the present disclosure.

One issue is image-level data waste. When medical images are acquired, the modality field of view (FOV) extends beyond the margins of the patient resulting in data waste. These useless components of a medical image file (e.g. DICOM file) can constitute up to 50% of the total pixels within the image file and are kept with the useful pare of the image in permanent storage. This unnecessary data results in increased storage costs, latency challenges, and difficulty in transmitting studies between institutions or just to client devices FIG. 13 depicts a block diagram 1300 re-illustrating a traditional medical imaging architecture as previously shown in FIG. 1. The block diagram 1300 further illustrates the redundant caching of complete images in accordance with embodiments of the present disclosure. The traditional medical imaging architecture including HIS/RIS 1302, a database gateway 1304, an image modality 1306, a PACS gateway 1308, a PACS server 1310, and display workstations 1312. Devices associated with the image modality 1306 may include X-ray devices, computed tomography (CT) scanners, magnetic resonance imaging (MRI) devices, and/or the like. Redundancy of images is shown in the image modality 1306, the PACS gateway 1308, and the PACS server 1310.

Figure 14:
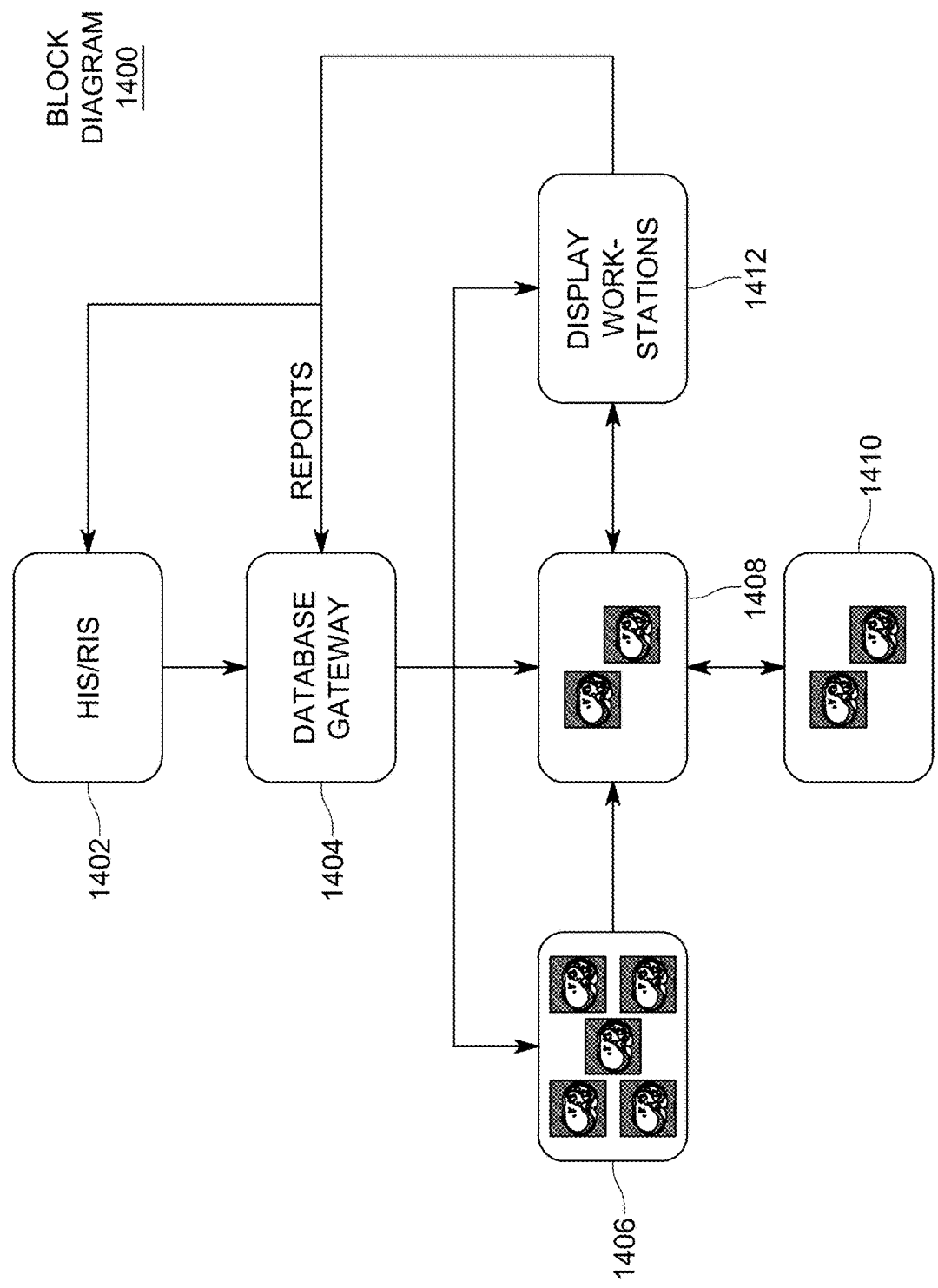
FIG. 14 depicts a block diagram illustrating a ZEBRE CLARITY™ solution for reducing non-useful data within medical imaging on an image series basis in accordance with embodiments of the present disclosure.

FIG. 14 depicts a block diagram 1400 illustrating an improved medical imaging architecture using a ZEBRE CLARITY™ solution for reducing non-useful data within medical imaging on an image series basis in accordance with embodiments of the present disclosure. The architecture includes an HIS/RIS 1402, a database gateway 1404, an image modality 1406, a ZEBRE CLARITY™ application 1408, a PACS server 1410, and display workstations 1420. The ZEBRE CLARITY™ application may be server based accessed via a web browser on a client device, client application based, or include a combination of specialized code operating on a server and a client device.

Figure 15:
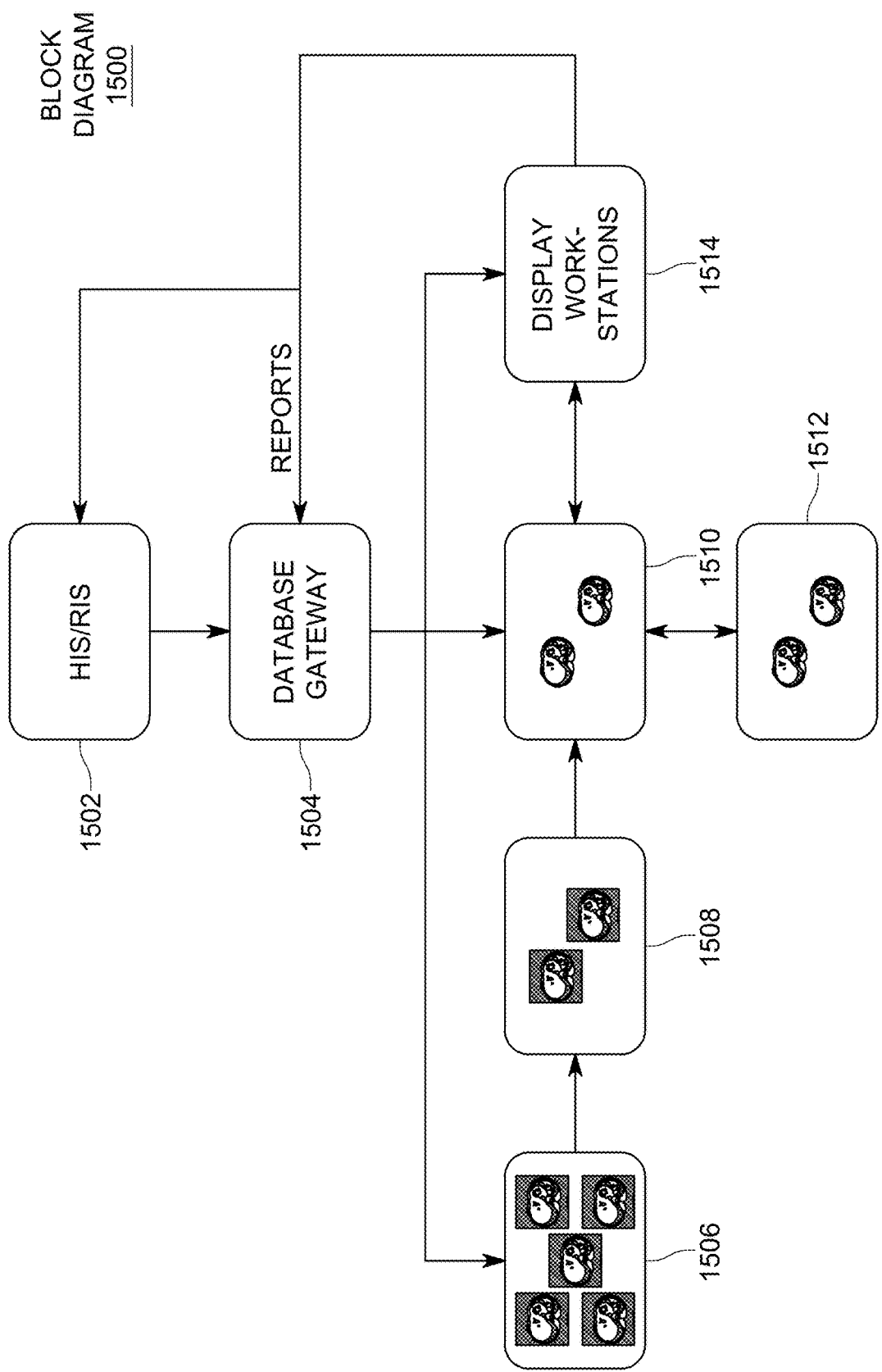
FIG. 15 depicts a block diagram illustrating the ZEBRE CLARITY™ solution for reducing non-useful data within medical imaging on an image series basis and a ZEBRE FOCUS™ solution for reducing non-useful data within medical imaging on a per image basis in accordance with embodiments of the present disclosure.

FIG. 15 depicts a block diagram 1500 illustrating and architecture using the ZEBRE CLARITY™ solution for reducing non-useful data within medical imaging on an image series basis and a ZEBRE FOCUS™ solution for reducing non-useful data within medical imaging on a per image basis in accordance with embodiments of the present disclosure. The architecture includes an HIS/RIS 1502, a database gateway 1504, an image modality 1506, a ZEBRE CLARITY™ application 1508, a ZEBRE FOCUS™ application 1510, a PACS server 1512, and display workstations 1514. The ZEBRE FOCUS™ application may be server based accessed via a web browser on a client device, client application based, or include a combination of specialized code operating on a server and a client device. Both the ZEBRE CLARITY™ solution and the ZEBRE FOCUS™ solution help to reduce the amount of memory used for caching large medical images during workflow while also reducing memory footprints for long term storage by removing non-useful data retained.

As an example of non-useful data in medical imaging, a CT scanner incorporates margins within CT images that extend beyond the patient resulting in diagnostically useless non-patient information being stored. Additionally, multiple images are captured providing a three-dimensional matrix of voxels producing even more non-useful information. To produce the three-dimensional matrix of voxels, the CT scanner using x-ray tubes and x-ray detectors that spin rapidly around a patient inside of a stationary ring called a gantry while the patient lies on a motorized table that moves rapidly through the gantry. The rotating X-ray tubes generate X-rays which pass through the patient and are detected by rotating x-ray detectors on the opposite side of the ring. The resulting data set is the three-dimensional matrix of voxels The ZEBRE FOCUS™ application reduces data waste by stripping non-diagnostic data from individual medical images across imaging modalities (including images from a CT scanner) via a multi-step process that (1) defines the margin of the patient, (2) establishes a safety buffer of approximately one centimeter around the margins of the patient, and (3) eliminates non-patient imaging data outside of the safety buffer. In some scenarios, the safety buffer may be approximately 0.1 to 0.6 centimeters. In other scenarios, the safety buffer may be approximately 0.5 to 1.1 centimeters. In still other scenarios, the safety buffer may be approximately 1.0 to 1.6 centimeters.

Figure 16:
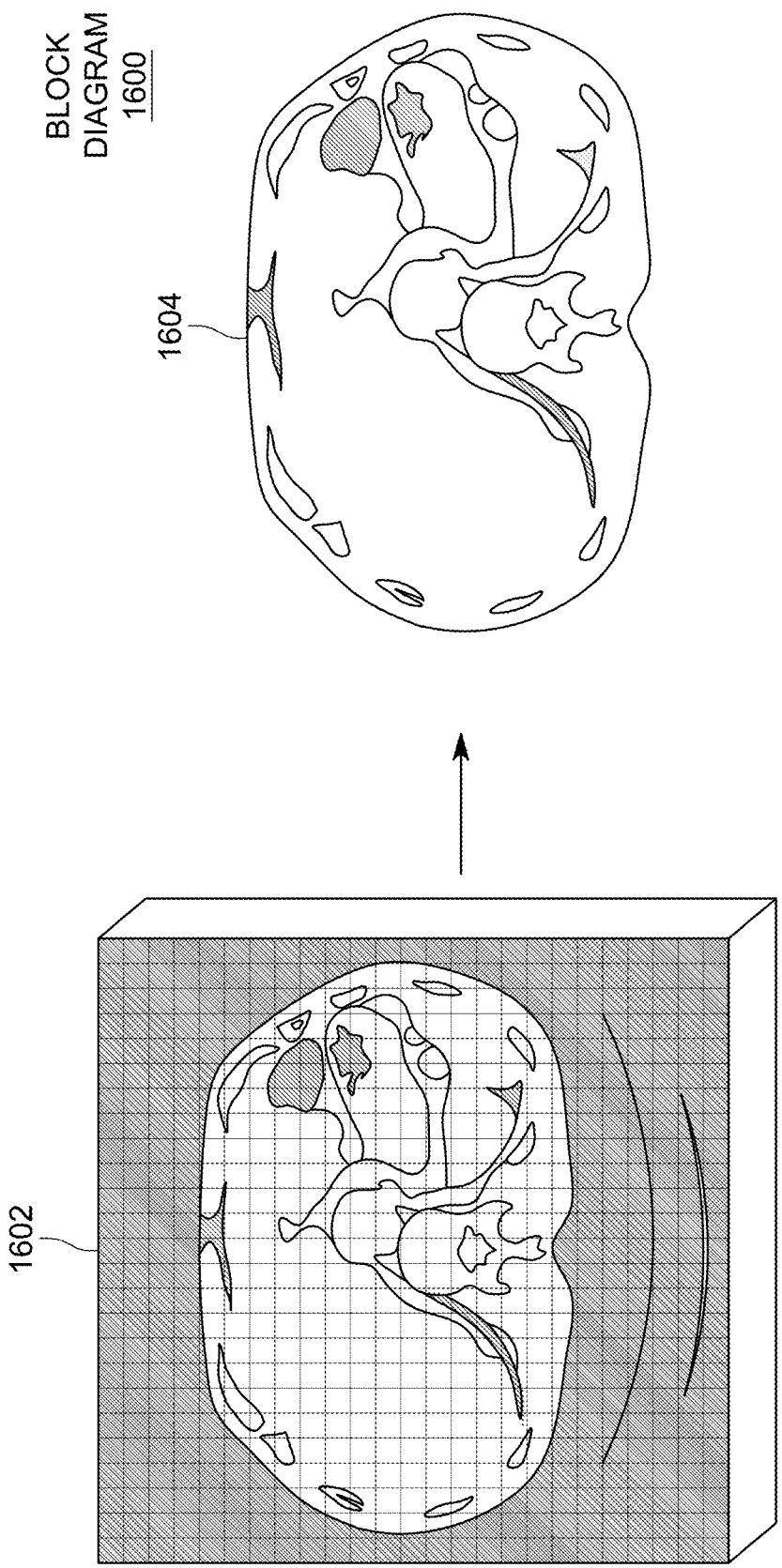
FIG. 16 depicts a diagram illustrating image reduction using transparency within the ZEBRE FOCUS™ solution in accordance with embodiments of the present disclosure.

FIG. 16 depicts a block diagram 1600 illustrating image reduction using transparency (i.e. the ZEBRE FOCUS™ application) in accordance with embodiments of the present disclosure. A first image 1602 of a three-dimensional matrix of voxels is depicted showing non-useful data captured by a CT scanner. A second image 1602 depicts the non-useful data removed using the ZEBRE FOCUS™ application. In certain embodiments, the safety buffer may be greater than one centimeter. In other embodiments, the safety buffer may be less that one centimeter. In certain embodiments, the safety buffer may be configured by a technician using the ZEBRE FOCUS™ application and/or other ZEBRE TECHNOLOGIES™ solution. In certain other embodiments AI and/or ML techniques may determine the safety buffer. The AI and/or ML techniques may use human-in-the-loop in determining the safety buffer. For example previous settings by the technician on similar images and/or diagnostic procedures may be used by AI and/or ML algorithms for setting the safety buffer. Additionally the technician may define the buffer using a selected template for a specific type of modality and/or body area to be imaged. The template may also be adjustable per a graphical user interface (GUI). For example the template may be associated with a lumbar MRI. Additionally, AI or ML may use metadata associated with an image or an image series to preselect or select the template to define the buffer.

Most all digital imaging modalities generate source image data/files that are then transformed into DICOM formatted images (or the like) that can be viewed for diagnostic purposes. Further manipulation of the DICOM images may be performed to generate series and/or "remixes" of the original DICOM images including multiplayer reformats (MPR), maximum intensity projection (MIP), three-dimensional reformats, and/or cine/video series. These generated series and/or "remixes can constitute 50 percent or more memory volume of the original study depending on the type of examination and institutional preferences.

Returning to the CT scanner example, a CT examination can include several different acquisitions of the same body part. This can occur when contrast is administered. From a primary one (thin axial) millimeter series, reformats "remixes" may be created that transform the thin axial series into thicker axial series (three to five millimeters), sagittal, coronal, maximum intensity projection (MIP) and three dimensional reconstructions. For example, a CT series of images of the chest abdomen and pelvis can include a non-contrast series (performed prior to contrast injection); an arterial phase series (triggered by contrast in the aorta to evaluate arterial structures and arterial hemorrhage); a venous phase series (timed after the arterial series to evaluate the enhancement of organs/tissues, venous structures, and venous hemorrhage); and a delayed series (to evaluate for delayed enhancement and contrast that has been excreted by the kidneys into the ureters and bladder). A "primary" thin axial series as described could generate twelve to fourteen additional series data sets on a post-processing workstation operated by a technologist at the site of the modality.

Figure 17:
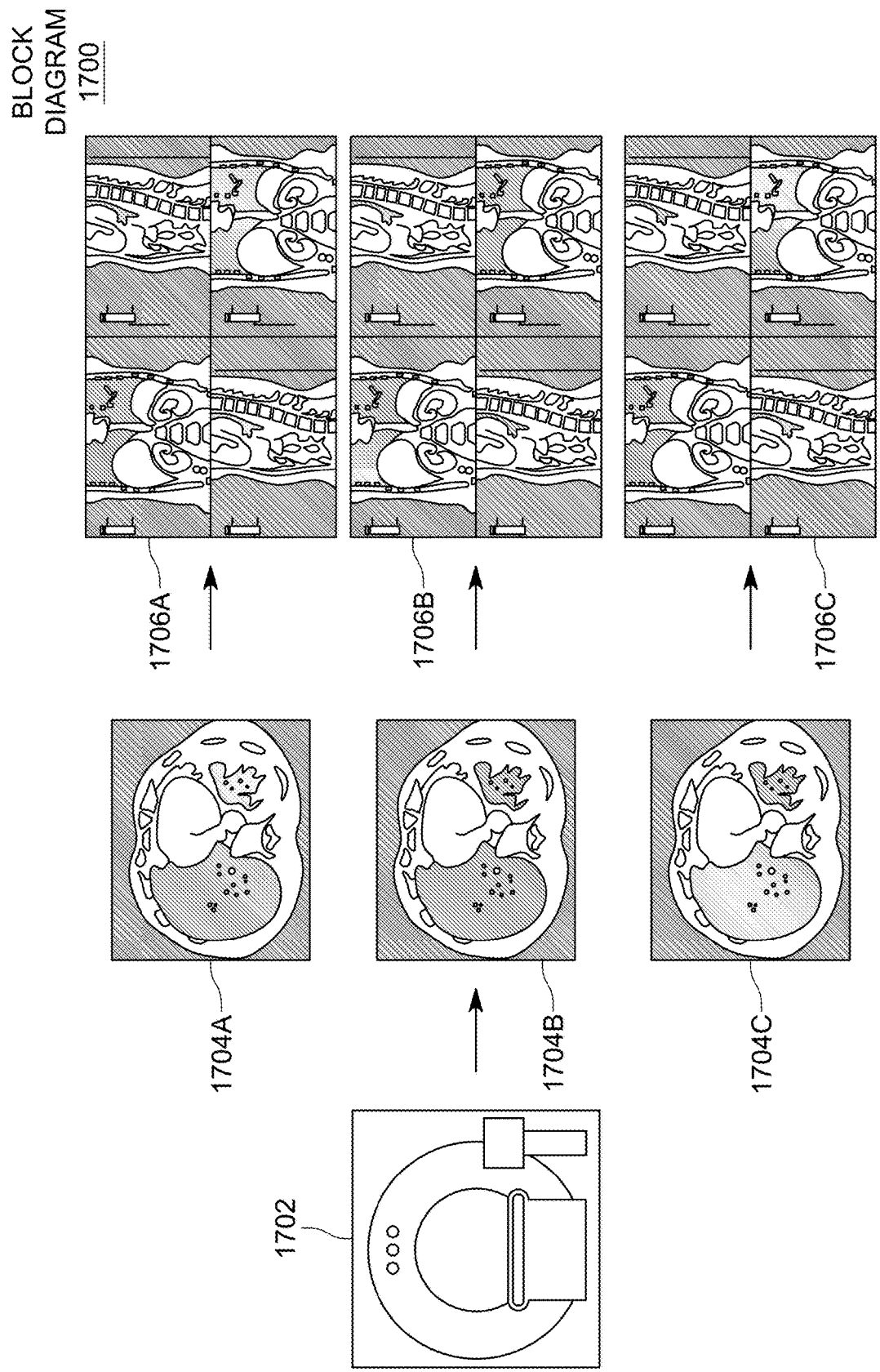
FIG. 17 depicts a diagram illustrating image replication producing non-novel data during a CT scan in accordance with embodiments of the present disclosure.

FIG. 17 depicts a block diagram 1700 illustrating image replication during a CT scan in accordance with embodiments of the present disclosure. As shown, a CT scanner 1702 during a single exam captures multiple thin axial original series images 1704A through 1704C and then creates numerous reformatted image series 1706A through 1706C that are basically remixes of the original imaging without novel data. In certain scenarios these remixes may produce as much as a 100 percent increase in the study size. These remixes are useful for a radiologist interpretation. However, they contain no novel data and utilize excess memory when stored in archives (e.g. DICOM servers, NVAs, etc.).

Figure 18:
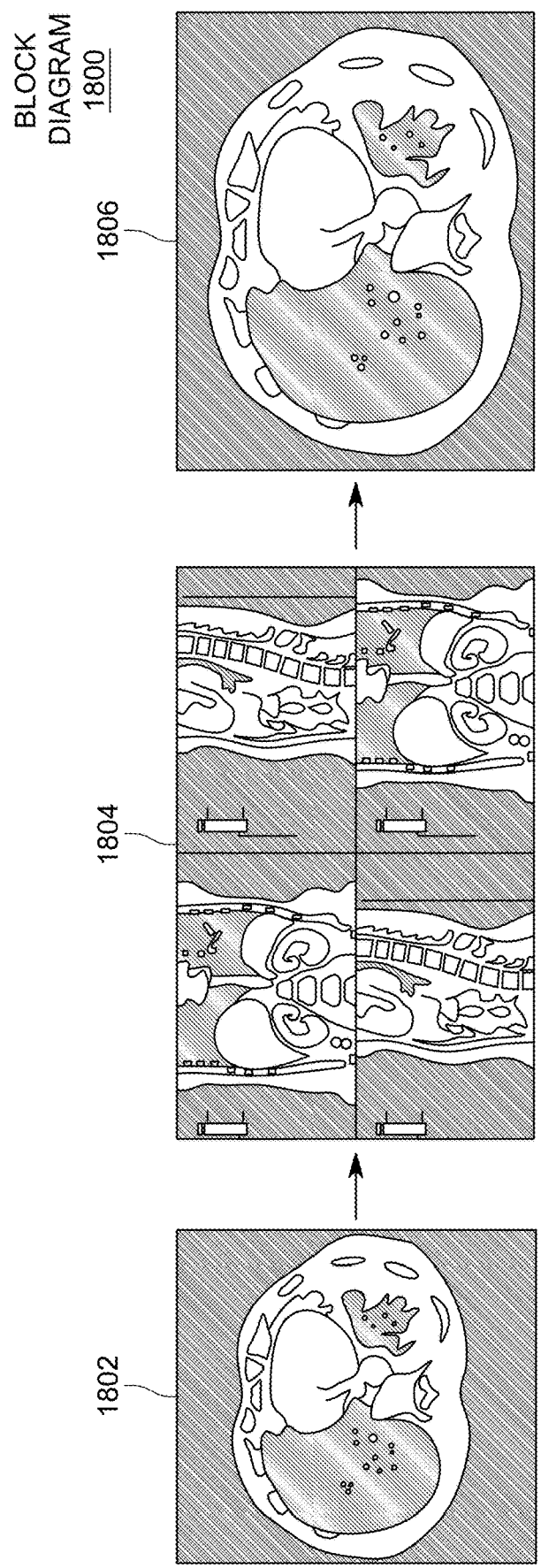
FIG. 18 depicts a diagram illustrating the ZEBRE CLARITY™ solution for reducing non-useful data within an image series originated from a CT scan in accordance with embodiments of the present disclosure.

FIG. 18 depicts a block diagram 1800 illustrating the ZEBRE CLARITY™ application for reducing non-useful data within an image series originated from a CT scan in accordance with embodiments of the present disclosure. An original image 1802 is captured as a one millimeter slice from a CT scanner. Reformats 1804 (and remixes) are created from the original image 1802 often times producing the 100 percent increase in the study size. As previously stated, the reformats 1804 are useful for radiologist interpretation but do not contain novel data. The ZEBRE CLARITY™ application identifies and eliminates reformatted image series (that do not contain any novel data), non-compliant studies, and non-diagnostic studies leaving the novel data as shown in image 1806 intact as the original image 1802. The non-compliant studies include outside studies erroneously imported, old studies no longer required to be retained, and/or the like. For non-diagnostic studies, the ZEBRE CLARITY™ application alerts a technologist and/or administrator that a study may contain excessive artifacts limiting diagnostic utility. The technologist and/or administrator may then be prompted to delete the excessive artifacts. In other embodiments, AI and ML may be used to automatically remove the excessive artifacts.

Another ZEBRE TECHNOLOGIES™ solution is the ZEBRE OPTIMIZE™ application. The ZEBRE OPTIMIZE™ application may be server based accessed via a web browser on a client device, client application based, or include a combination of specialized code operating on a server and a client device. The ZEBRE OPTIMIZE™ application includes a ZEBRE OPTIMIZE™ artifact analysis engine and a ZEBRE OPTIMIZE™ compliance analysis engine. Imaging artifacts (e.g. motion artifacts) can significantly reduce the diagnostic utility of radiology examinations. The ZEBRE OPTIMIZE™ artifact reduction engine identifies artifacts and provides real-time feedback to the technologist indicating when the artifact occurred. The ZEBRE OPTIMIZE™ compliance analysis engine allows institutions to implement national, federal, local and institution-specific image retention and storage guidelines to ensure that they are retaining medical imaging studies that should be retained and purging examinations that are not in compliance with regulatory and institutional policy frameworks.

The ZEBRE OPTIMIZE™ application may be utilized in multiple ways. This includes automated use of the ZEBRE FOCUS™ application and the ZEBRE CLARITY™ application at the time of medical image acquisition. Additionally, retrospective use of the ZEBRE FOCUS™ application and the ZEBRE CLARITY™ application can be user to "scrub" image archives.

Figure 19:
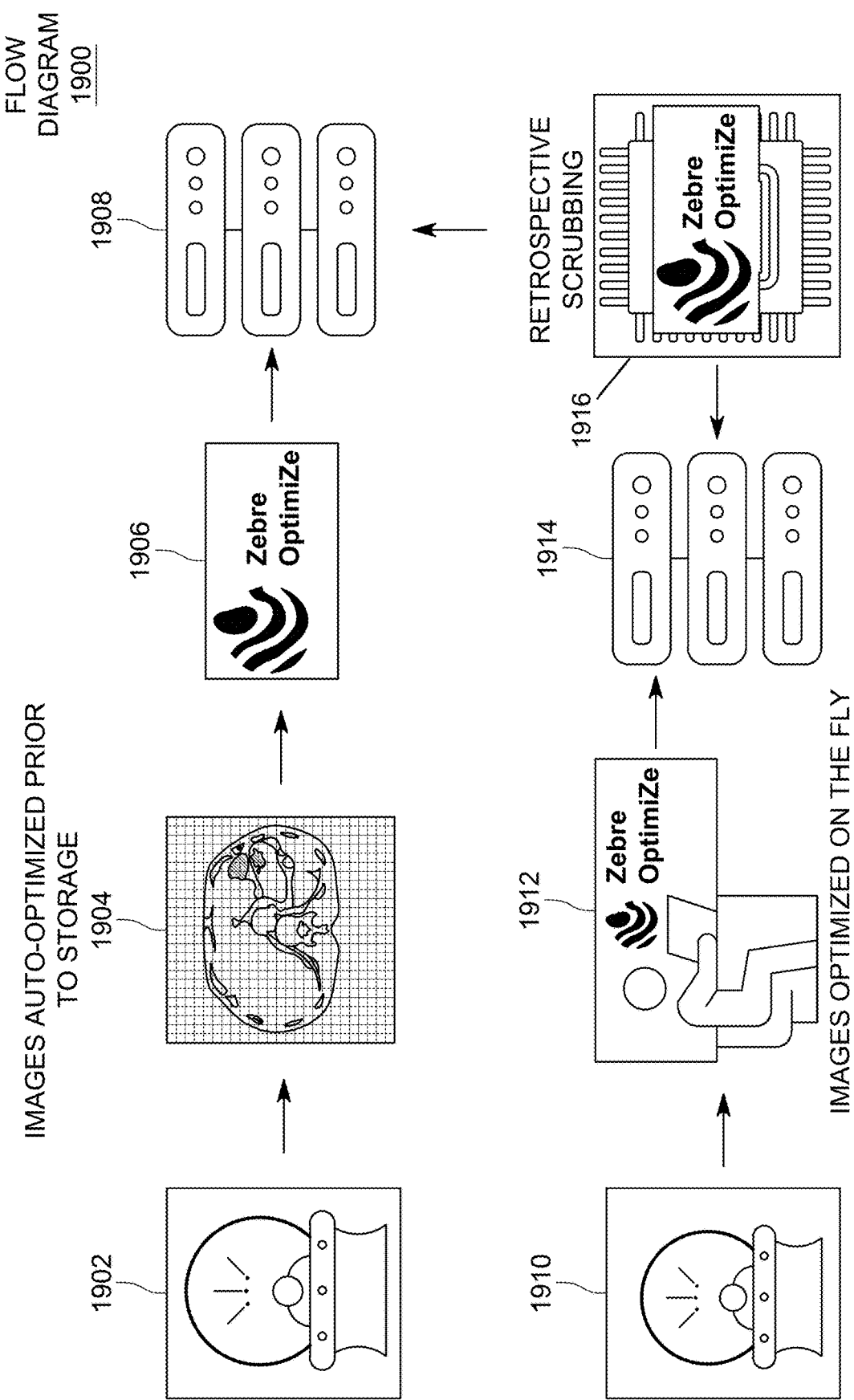
FIG. 19 depicts a flow diagram illustrating CT images auto-optimized prior to storage and CT images optimized by a technician on-the-fly using a ZEBRE OPTIMIZE™ application in accordance with embodiments of the present disclosure.

FIG. 19 depicts a flow diagram 1900 illustrating CT images auto-optimized prior to storage and CT images optimized by a technician on-the-fly in accordance with embodiments of the present disclosure. A CT scanner 1902 provides source images 1904 to a ZEBRE OPTIMIZE™ application 1906 for auto executing a ZEBRE CLARITY™ application and/or a ZEBRE FOCUS™ application before submitting to storage 1908 (i.e. images auto-optimized prior to storage). Another CT scanner 1910 provides image to a technologist using the ZEBRE OPTIMIZE™ application 1924 before submitting "on-the-fly" to storage 1914. The technologist may implement a ZEBRE CLARITY™ application and/or a ZEBRE FOCUS™ application before submitting to storage 1914. Additionally, a ZEBRE OPTIMIZE™ application 1916 for retrospective scrubbing of images using a ZEBRE CLARITY™ application and/or a ZEBRE FOCUS™ application before re-submitting to storage 1908 and/or storage 1914.

Figure 20:
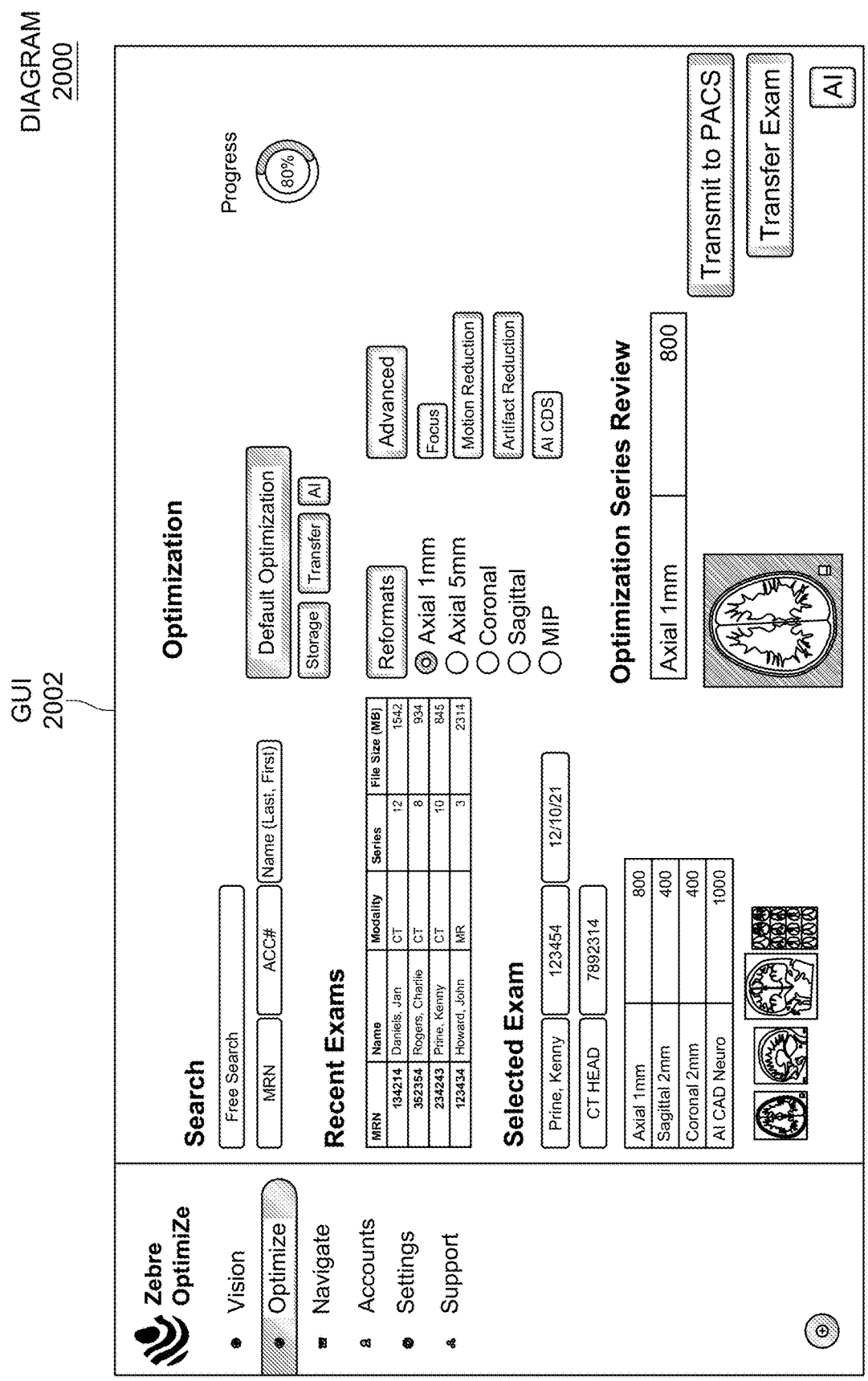
FIG. 20 depicts a diagram illustrating a GUI within the ZEBRE OPTIMIZE™ application in accordance with embodiments of the present disclosure.

FIG. 20 depicts a diagram 2000 illustrating a GUI 2002 for a ZEBRE OPTIMIZE™ application in accordance with embodiments of the present disclosure. The GUI 2002 provides a manual interface for optimization (e.g. "on-the-fly" optimization and or retrospective scrubbing by the technician as disclosed in FIG. 19. The GUI 2002 provides the technician the ability to search for exams as well as access recent exams. The GUI 2002 also provides for review of per image or image series optimization before submitting.

Also within the ZEBRE TECHNOLOGIES™ solutions are ZEBRE FLOW™ solutions including multiple workflow oriented applications designed to enable utilization of medical images across key steps in medical imaging workflow. The ZEBRE FLOW™ solutions include a ZEBRE VISION™ application, a ZEBRE COORDINATE™ application, and a ZEBRE NAVIGATE™ application.

The ZEBRE VISION™ application enables the manipulation of images generated by the ZEBRE OPTIMIZE™ application, as well as standard non-optimized DICOM files for diagnostic imaging purposes. The ZEBRE VISION™ application may be server based accessed via a web browser on a client device, client application based, or include a combination of specialized code operating on a server and a client device.

The ZEBRE COORDINATE™ application enables the remote transfer of medical images generated by the ZEBRE OPTIMIZE™ application across multiple medical facilities. The ZEBRE OPTIMIZE™ application may be server based accessed via a web browser on a client device, client application based, or include a combination of specialized code operating on a server and a client device.

The ZEBRE NAVIGATE™ application provides an administrative portal for system-level storage analysis, workflow protocol rules, retention guidelines, and related metrics—including estimates of carbon footprint savings related to medical imaging. The ZEBRE NAVIGATE™ application may be server based accessed via a web browser on a client device, client application based, or include a combination of specialized code operating on a server and a client device.

The ZEBRE VISION™ application transforms ZEBRE OPTIMIZE™ files into customized formats for diagnostic interpretation, post-processing applications (including AI/ML applications), and other uses—including research-focused applications. The ZEBRE NAVIGATE™ application may be server based accessed via a web browser on a client device, client application based, or include a combination of specialized code operating on a server and a client device.

Figure 21:
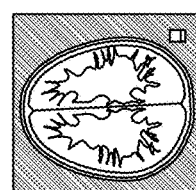
FIG. 21 depicts a diagram illustrating another GUI within a ZEBRE VISION™ application in accordance with embodiments of the present disclosure

This The ZEBRE VISION™ application allows for on-the-fly reconstructions of series that have been optimized for data storage using the ZEBRE OPTIMIZE™ application beyond what is created "behind the scenes" by automated reconstruction series that are generated when a study is pulled out of archive for retrieval. Reconstructed series can be reviewed before sending to PACS using a built-in non-diagnostic imaging viewer. FIG. 21 depicts a diagram 2100 illustrating a GUI 2102 for the ZEBRE VISION™ application in accordance with embodiments of the present disclosure The ZEBRE COORDINATE™ application is a lightweight version of ZEBRE VISION™ application that allows for outside medical institutions and other entities that are not using the previously disclosed the ZEBRE TECHNOLOGIES™ solutions to receive ZEBRE optimized images from ZEBRE clients using the ZEBRE OPTIMIZE™ application (e.g. study transfer). The ZEBRE COORDINATE™ application may be server based accessed via a web browser on a client device, client application based, or include a combination of specialized code operating on a server and a client device. The ZEBRE COORDINATE™ application functions in a similar fashion to built-in auto-launch viewers that are currently included with diagnostic imaging studies transmitted between different medical institutions via compact disc (CD).

If an outside medical institution that is requesting images from a Zebre client chooses not to use the ZEBRE COORDINATE™ application, these reformats can be created prior to transfer of the images at the originating medical facility and then transmitted to the outside medical facility. This workflow, however, is suboptimal as it requires transfer of unnecessarily large file sizes. FIG. 22 depicts a diagram 2200 illustrating a GUI 2202 for the ZEBRE COORDINATE™ application in accordance with embodiments of the present disclosure.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including object oriented and/or procedural programming languages. For example, programming languages may include, but are not limited to: Ruby, JavaScript, Java, Python, Ruby, PHP, C, C++, C#, Objective-C, Go, Scala, Swift, Kotlin, OCaml, or the like.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method implemented on at least one computing device for management of medical imaging, the method comprising:
   receiving a source medical image file from a first remote device;
   caching the source medical image file in local memory;
   determining relevant medical image data, first non-relevant medical image data, and second non-relevant medical image data within the source medical image file;
   removing the second non-relevant medical image data to create a memory reduced medical image file;
   storing the memory reduced medical image file in the local memory; and
   transmitting the memory reduced medical image file to a second remote device.

2. The method of claim 1 further, wherein the first non-relevant medical image data includes a buffer positioned around the relevant medical image data.

3. The method of claim 1 further comprising replacing the second non-relevant medical image data with a transparent background.

4. The method of claim 3, wherein the second remote device is configured to replace the transparent background with a solid background to create a memory expanded medical image file compliant to an image format of the source medical image file.

5. The method of claim 4, wherein the solid background is a substantially black background.

6. The method of claim 1, wherein determining the relevant medical image data, the first non-relevant medical image data, and the second non-relevant medical image data within the source medical image file comprises machine learning.

7. The method of claim 1, wherein the second remote device is a picture archiving and communication system (PACS) server, and the at least one computing device is a PACS caching gateway server.

8. The method of claim 1, wherein the memory reduced medical image file yields a greater than 50 percent digital data reduction over the source medical image file.

9. The method of claim 1, wherein the first remote device is an image modality device.

10. The method of claim 9, wherein the image modality device is at least one of an X-ray device, a computed tomography (CT) scanner, and a magnetic resonance imaging (MRI) device.

11. The method of claim 1, wherein the second remote device includes a PACS viewer.

12. The method of claim 1, wherein the source medical image file is compliant to at least one version of a Digital Imaging and Communications in Medicine (DICOM) format.

13. The method of claim 1, wherein the source medical image file is compliant to at least one version of a Neuroimaging Informatics Technology Initiative (NIfTI) format.

14. The method of claim 1, wherein the source medical image file is based on at least one of X-ray radiography, magnetic resonance imaging, ultrasound, endoscopy, elastography, tactile imaging, thermography, medical photography, and a nuclear medicine functional imaging technique.

15. The method of claim 1, wherein the source medical image file is based on non-image data.

16. The method of claim 15, wherein the non-image data is at least one of graphing data and mapping data.

17. The method of claim 15, wherein the non-image data is captured using at least one of electroencephalography (EEG), magnetoencephalography (MEG), and electrocardiography (ECG).

18. The method of claim 1, wherein the second remote device is at least one of a medical diagnostic workstation, a personal computer, a smart phone, a smart tablet, a smart watch, a smart television (TV), a holographic projector, a two dimensional printer, a three dimensional printer, and a transfer device for a portable storage device.

19. A computing device for comprising:
a memory; and
at least one processor configured for:
receiving a source medical image file from a first remote device;
caching the source medical image file in local memory;
determining relevant medical image data, first non-relevant medical image data, and second non-relevant medical image data within the source medical image file;
removing the second non-relevant medical image data to create a memory reduced medical image file;
storing the memory reduced medical image file in the local memory; and
transmitting the memory reduced medical image file to a second remote device.

20. A non-transitory computer-readable storage medium, the non-transitory computer-readable storage medium storing instructions to be implemented on at least one computing device including at least one processor, the instructions when executed by the at least one processor to perform a method of:
receiving a source medical image file from a first remote device;
caching the source medical image file in local memory;
determining relevant medical image data, first non-relevant medical image data, and second non-relevant medical image data within the source medical image file; and
removing the second non-relevant medical image data to create a memory reduced medical image file;
storing the memory reduced medical image file in the local memory; and
transmitting the memory reduced medical image file to a second remote device.

* * * * *